United States Patent
Tollefson

(10) Patent No.: US 11,324,741 B2
(45) Date of Patent: May 10, 2022

(54) METHODS FOR TREATING VISCERAL FAT CONDITIONS

(71) Applicant: Orexigen Therapeutics, Inc., La Jolla, CA (US)

(72) Inventor: Gary D. Tollefson, Indianapolis, IN (US)

(73) Assignee: Nalpropion Pharmaceuticals LLC, Morristown, NJ (US)

( * ) Notice: Subject to any disclaimer, the term of this patent is extended or adjusted under 35 U.S.C. 154(b) by 0 days.

(21) Appl. No.: 15/446,933

(22) Filed: Mar. 1, 2017

(65) Prior Publication Data

US 2017/0172999 A1 Jun. 22, 2017

Related U.S. Application Data

(63) Continuation of application No. 14/584,985, filed on Dec. 29, 2014, now abandoned, which is a continuation of application No. 12/995,121, filed as application No. PCT/US2009/045720 on May 29, 2009, now abandoned.

(60) Provisional application No. 61/057,743, filed on May 30, 2008.

(51) Int. Cl.
*A61K 31/485* (2006.01)
*A61K 31/137* (2006.01)

(52) U.S. Cl.
CPC .......... *A61K 31/485* (2013.01); *A61K 31/137* (2013.01)

(58) Field of Classification Search
None
See application file for complete search history.

(56) References Cited

U.S. PATENT DOCUMENTS

| | | |
|---|---|---|
| 3,819,706 A | 6/1974 | Mehta |
| 3,885,046 A | 5/1975 | Mehta |
| 3,942,641 A | 3/1976 | Segre |
| 4,089,855 A | 5/1978 | Chatterjie et al. |
| 4,172,896 A | 10/1979 | Uno et al. |
| 4,218,433 A | 8/1980 | Kooichi et al. |
| 4,295,567 A | 10/1981 | Knudsen |
| 4,451,465 A | 5/1984 | White et al. |
| 4,483,846 A | 11/1984 | Koide et al. |
| 4,513,006 A | 4/1985 | Maryanoff et al. |
| 4,673,679 A | 6/1987 | Aungst et al. |
| 4,689,332 A | 8/1987 | McLaughlin et al. |
| 4,828,836 A | 5/1989 | Elger et al. |
| 4,831,031 A | 5/1989 | Lowe et al. |
| 4,855,306 A | 8/1989 | Markstein et al. |
| 4,895,845 A | 1/1990 | Seed |
| 5,000,886 A | 3/1991 | Lawter et al. |
| 5,028,612 A | 7/1991 | Glover |
| 5,082,864 A | 1/1992 | Van den Oetelaar et al. |
| 5,202,128 A | 4/1993 | Morella et al. |
| 5,213,807 A | 5/1993 | Chemburkar et al. |
| 5,213,808 A | 5/1993 | Bar-Shalom et al. |
| 5,283,263 A | 2/1994 | Norden |
| 5,312,925 A | 5/1994 | Allen et al. |
| 5,358,970 A | 10/1994 | Ruff et al. |
| 5,364,841 A | 11/1994 | Cooper et al. |
| 5,403,595 A | 4/1995 | Kitchell et al. |
| 5,426,112 A | 6/1995 | Zagon et al. |
| 5,427,798 A | 6/1995 | Ludwig et al. |
| 5,486,362 A | 1/1996 | Kitchell et al. |
| 5,512,593 A | 4/1996 | Dante |
| 5,541,231 A | 7/1996 | Ruff et al. |
| 5,626,874 A | 5/1997 | Conte et al. |
| 5,714,519 A | 2/1998 | Cincotta et al. |
| 5,716,976 A | 2/1998 | Bernstein |
| 5,719,197 A | 2/1998 | Kanios et al. |
| 5,731,000 A | 3/1998 | Ruff et al. |
| 5,738,874 A | 4/1998 | Conte et al. |
| 5,763,493 A | 6/1998 | Ruff et al. |
| 5,817,665 A | 10/1998 | Dante |
| 5,817,666 A | 10/1998 | Katz |
| 5,856,332 A | 1/1999 | Dante |
| 5,866,164 A | 2/1999 | Kuczynski et al. |
| 5,948,799 A | 9/1999 | Cropp |
| 5,958,962 A | 9/1999 | Cook |
| 5,977,099 A | 11/1999 | Nickolson |
| 6,004,970 A | 12/1999 | O'Malley et al. |
| 6,033,686 A | 3/2000 | Seth |
| 6,034,091 A | 3/2000 | Dante |
| 6,048,322 A | 4/2000 | Kushida |
| 6,071,537 A | 6/2000 | Shank |
| 6,071,918 A | 6/2000 | Cook |
| 6,087,386 A | 7/2000 | Chen et al. |
| 6,096,341 A | 8/2000 | Seth |

(Continued)

FOREIGN PATENT DOCUMENTS

| CA | 2317044 | 7/1999 |
|---|---|---|
| EP | 0 005 636 | 11/1979 |

(Continued)

OTHER PUBLICATIONS

Eckel et al. ("Eckel") The Lancet 365, 2005, 1415-1428; (Year: 2005).*
Kuk et al. ("Kuk") Obesity 14(2), 2006, 336-341; (Year: 2006).*
Janssen et al. ("Janssen") International Journal of Obesity 23, 1999, 1035-1046 (Year: 1999).*
Van Gaal et al ("Van Gaal") International Journal of Obesity Related Metabolic Disorders 1998, 22, Abstract; (Year: 1998).*
Casado et al. ("Casado") Nutrition Neuroscience 6(2) 2003, Abstract. (Year: 2003).*
Vidal J., International Journal of Obesity (2002) 26, Suppl 4, S25-S28; (Year: 2002).*

(Continued)

*Primary Examiner* — Jeffrey S Lundgren
*Assistant Examiner* — Michael J Schmitt
(74) *Attorney, Agent, or Firm* — Servilla Whitney LLC

(57) ABSTRACT

Disclosed are methods and compositions for treating visceral fat conditions and/or metabolic syndrome using combinations of naltrexone and bupropion.

18 Claims, 1 Drawing Sheet

(56) References Cited

U.S. PATENT DOCUMENTS

| | | |
|---|---|---|
| 6,110,973 A | 8/2000 | Young |
| 6,120,803 A | 9/2000 | Wong et al. |
| 6,143,327 A | 11/2000 | Seth |
| 6,150,366 A | 11/2000 | Arenson et al. |
| 6,153,223 A | 11/2000 | Apelian et al. |
| 6,183,778 B1 | 2/2001 | Conte et al. |
| 6,191,117 B1 | 2/2001 | Kozachuk |
| 6,197,827 B1 | 3/2001 | Cary |
| 6,210,716 B1 | 4/2001 | Chen et al. |
| 6,238,697 B1 | 5/2001 | Kumar et al. |
| 6,245,766 B1 | 6/2001 | Watsky |
| 6,248,363 B1 | 6/2001 | Patel et al. |
| 6,262,049 B1 | 7/2001 | Coffin et al. |
| 6,274,579 B1 | 8/2001 | Morgan et al. |
| 6,294,192 B1 | 9/2001 | Patel et al. |
| 6,306,436 B1 | 10/2001 | Chungi et al. |
| 6,323,236 B2 | 11/2001 | McElroy |
| 6,342,496 B1 | 1/2002 | Jerussi et al. |
| 6,342,515 B1 | 1/2002 | Masuda et al. |
| 6,344,474 B1 | 2/2002 | Maruani et al. |
| 6,362,220 B1 | 3/2002 | Cottrell |
| 6,369,113 B2 | 4/2002 | Young |
| 6,383,471 B1 | 5/2002 | Chen et al. |
| 6,387,956 B1 | 5/2002 | Shapira |
| 6,420,369 B1 | 7/2002 | Marcotte |
| 6,437,147 B1 | 8/2002 | Andersen et al. |
| 6,441,038 B1 | 8/2002 | Loder et al. |
| 6,451,860 B1 | 9/2002 | Young |
| 6,462,237 B1 | 10/2002 | Gidwani et al. |
| 6,500,459 B1 | 12/2002 | Chhabra et al. |
| 6,506,799 B1 | 1/2003 | Dasseux |
| 6,514,531 B1 | 2/2003 | Alaux et al. |
| 6,528,520 B2 | 3/2003 | Clemens |
| 6,541,478 B1 | 4/2003 | O'Malley et al. |
| 6,548,551 B2 | 4/2003 | Hinz |
| 6,569,449 B1 | 5/2003 | Stinchcomb et al. |
| 6,576,256 B2 | 6/2003 | Liang et al. |
| 6,589,553 B2 | 7/2003 | Li et al. |
| 6,622,036 B1 | 9/2003 | Suffin |
| 6,627,223 B2 | 9/2003 | Percel et al. |
| 6,630,165 B2 | 10/2003 | Seroff et al. |
| 6,638,535 B2 | 10/2003 | Lemmens et al. |
| 6,652,882 B1 | 11/2003 | Odidi et al. |
| 6,682,759 B2 | 1/2004 | Lim et al. |
| 6,686,337 B2 | 2/2004 | Connor |
| 6,706,283 B1 | 3/2004 | Appel et al. |
| 6,713,488 B2 | 3/2004 | Sadee et al. |
| 6,797,283 B1 | 9/2004 | Edgren et al. |
| 6,893,660 B2 | 5/2005 | Li et al. |
| 6,893,661 B1 | 5/2005 | Odidi et al. |
| 6,905,708 B2 | 6/2005 | Li et al. |
| 6,923,988 B2 | 8/2005 | Patel et al. |
| 6,926,907 B2 | 8/2005 | Plachetka |
| 6,995,169 B2 | 2/2006 | Chapleo et al. |
| 7,109,198 B2 | 9/2006 | Gadde et al. |
| 7,375,111 B2 | 5/2008 | Weber et al. |
| 7,422,110 B2 | 9/2008 | Zanden et al. |
| 7,425,571 B2 | 9/2008 | Gadde et al. |
| 7,429,580 B2 | 9/2008 | Gadde et al. |
| 7,462,626 B2 | 12/2008 | Weber et al. |
| 7,682,633 B2 | 3/2010 | Matthews et al. |
| 7,754,748 B2 | 7/2010 | Gadde et al. |
| 8,088,786 B2 | 1/2012 | McKinney et al. |
| 8,318,788 B2 | 11/2012 | McKinney et al. |
| 8,722,085 B2 | 5/2014 | McKinney et al. |
| 8,815,889 B2 | 8/2014 | Cowley et al. |
| 8,916,195 B2 | 12/2014 | McKinney et al. |
| 8,969,371 B1 | 3/2015 | Klassen et al. |
| 9,107,837 B2 | 8/2015 | McKinney et al. |
| 9,119,850 B2 | 9/2015 | Klassen et al. |
| 9,125,868 B2 | 9/2015 | McKinney et al. |
| 9,248,123 B2 | 2/2016 | Dunayevich et al. |
| 9,457,005 B2 | 10/2016 | Cowley et al. |
| 9,633,575 B2 | 4/2017 | Klassen et al. |
| 2001/0025038 A1 | 9/2001 | Coffin et al. |
| 2001/0046964 A1 | 11/2001 | Percel et al. |
| 2002/0012680 A1 | 1/2002 | Patel et al. |
| 2002/0019364 A1 | 2/2002 | Renshaw |
| 2002/0022054 A1 | 2/2002 | Sawada et al. |
| 2002/0025972 A1 | 2/2002 | Hintz |
| 2002/0037836 A1 | 3/2002 | Henriksen |
| 2002/0044962 A1 | 4/2002 | Cherukuri et al. |
| 2002/0055512 A1 | 5/2002 | Marin et al. |
| 2002/0090615 A1 | 7/2002 | Rosen et al. |
| 2002/0132850 A1 | 9/2002 | Bartholomaeus et al. |
| 2002/0198227 A1 | 12/2002 | Bernstein |
| 2003/0003151 A1 | 1/2003 | Chopra |
| 2003/0017189 A1 | 1/2003 | Wong et al. |
| 2003/0035840 A1 | 2/2003 | Li et al. |
| 2003/0044462 A1 | 3/2003 | Subramanian et al. |
| 2003/0054031 A1 | 3/2003 | Li et al. |
| 2003/0054041 A1 | 3/2003 | Lemmens et al. |
| 2003/0055008 A1 | 3/2003 | Marcotte |
| 2003/0055038 A1 | 3/2003 | Howard et al. |
| 2003/0068371 A1 | 4/2003 | Oshlack et al. |
| 2003/0087896 A1 | 5/2003 | Glover |
| 2003/0091630 A1 | 5/2003 | Louie-Helm et al. |
| 2003/0109546 A1 | 6/2003 | Fenton |
| 2003/0130322 A1 | 7/2003 | Howard |
| 2003/0133982 A1 | 7/2003 | Heimlich et al. |
| 2003/0133985 A1 | 7/2003 | Louie-Helm et al. |
| 2003/0135056 A1 | 7/2003 | Anderson et al. |
| 2003/0144174 A1 | 7/2003 | Brenna et al. |
| 2003/0144271 A1 | 7/2003 | Shulman |
| 2003/0147952 A1 | 8/2003 | Lim et al. |
| 2003/0161874 A1 | 8/2003 | Li et al. |
| 2003/0198683 A1 | 10/2003 | Li et al. |
| 2003/0215496 A1 | 11/2003 | Patel et al. |
| 2004/0002462 A1 | 1/2004 | Najarian |
| 2004/0005368 A1 | 1/2004 | Mann et al. |
| 2004/0022852 A1 | 2/2004 | Chopra |
| 2004/0029941 A1 | 2/2004 | Jennings |
| 2004/0047908 A1 | 3/2004 | Lemmens et al. |
| 2004/0059241 A1 | 3/2004 | Suffin |
| 2004/0092504 A1 | 5/2004 | Benja-Athon |
| 2004/0096499 A1 | 5/2004 | Vaya et al. |
| 2004/0101556 A1 | 5/2004 | Li et al. |
| 2004/0105778 A1 | 6/2004 | Lee et al. |
| 2004/0106576 A1 | 6/2004 | Jerussi et al. |
| 2004/0115134 A1 | 6/2004 | Merisko-Liversidge |
| 2004/0122033 A1 | 6/2004 | Nargund et al. |
| 2004/0158194 A1 | 8/2004 | Wolff et al. |
| 2004/0185097 A1 | 9/2004 | Kannan et al. |
| 2004/0204472 A1 | 10/2004 | Briggs et al. |
| 2004/0228915 A1 | 11/2004 | Noack et al. |
| 2004/0228924 A1 | 11/2004 | Oshlack et al. |
| 2004/0242974 A1 | 12/2004 | Glover |
| 2004/0258757 A1 | 12/2004 | Bosch et al. |
| 2005/0004106 A1 | 1/2005 | Romano |
| 2005/0013863 A1 | 1/2005 | Lim et al. |
| 2005/0019385 A1 | 1/2005 | Houze |
| 2005/0019409 A1 | 1/2005 | Edgren et al. |
| 2005/0019412 A1 | 1/2005 | Bosch et al. |
| 2005/0026977 A1 | 2/2005 | Jennings |
| 2005/0026986 A1 | 2/2005 | Maruani et al. |
| 2005/0031691 A1 | 2/2005 | McGurk et al. |
| 2005/0043704 A1 | 2/2005 | Lieberburg |
| 2005/0043705 A1 | 2/2005 | Lieberburg |
| 2005/0043773 A1 | 2/2005 | Lieberburg |
| 2005/0063913 A1 | 3/2005 | Pruitt et al. |
| 2005/0096311 A1 | 5/2005 | Suffin et al. |
| 2005/0112198 A1 | 5/2005 | Challapalli et al. |
| 2005/0112211 A1 | 5/2005 | Gervais et al. |
| 2005/0118268 A1 | 6/2005 | Percel et al. |
| 2005/0137144 A1 | 6/2005 | Gadde et al. |
| 2005/0142195 A1 | 6/2005 | Li et al. |
| 2005/0143322 A1 | 6/2005 | Gadde et al. |
| 2005/0147664 A1 | 7/2005 | Liversidge et al. |
| 2005/0154002 A1 | 7/2005 | Crooks et al. |
| 2005/0163840 A1 | 7/2005 | Sawada et al. |
| 2005/0169990 A1 | 8/2005 | Kao et al. |
| 2005/0181049 A1 | 8/2005 | Dong et al. |
| 2005/0214368 A1 | 9/2005 | Kawakami et al. |
| 2005/0214371 A1 | 9/2005 | Di Capua et al. |

(56) References Cited

U.S. PATENT DOCUMENTS

| | | |
|---|---|---|
| 2005/0214372 A1 | 9/2005 | Di Capua et al. |
| 2005/0215552 A1 | 9/2005 | Gadde et al. |
| 2005/0232990 A1 | 10/2005 | Boehm et al. |
| 2005/0238718 A1 | 10/2005 | Oberegger et al. |
| 2005/0245460 A1 | 11/2005 | Meyerson et al. |
| 2005/0250838 A1 | 11/2005 | Challapalli et al. |
| 2005/0277579 A1 | 12/2005 | Gadde et al. |
| 2006/0009514 A1 | 1/2006 | Gadde et al. |
| 2006/0018933 A1 | 1/2006 | Vaya et al. |
| 2006/0018934 A1 | 1/2006 | Vaya et al. |
| 2006/0024365 A1 | 2/2006 | Vaya et al. |
| 2006/0051418 A1 | 3/2006 | Cowen et al. |
| 2006/0058293 A1 | 3/2006 | Weber et al. |
| 2006/0069086 A1 | 3/2006 | Michalow |
| 2006/0079501 A1 | 4/2006 | Gadde et al. |
| 2006/0100205 A1 | 5/2006 | Weber et al. |
| 2006/0122127 A1 | 6/2006 | Rao et al. |
| 2006/0142290 A1* | 6/2006 | Weber ............ A61K 31/135 514/238.8 |
| 2006/0160750 A1 | 7/2006 | Gadde et al. |
| 2006/0246131 A1 | 11/2006 | Cottinham |
| 2006/0276412 A1 | 12/2006 | Tollefson |
| 2007/0078135 A1 | 4/2007 | Yuan et al. |
| 2007/0099947 A1 | 5/2007 | Dean et al. |
| 2007/0117827 A1 | 5/2007 | Tollefson et al. |
| 2007/0129283 A1 | 6/2007 | McKinney et al. |
| 2007/0148237 A1 | 6/2007 | McKinney et al. |
| 2007/0149451 A1 | 6/2007 | Holmes |
| 2007/0179168 A1 | 8/2007 | Cowley et al. |
| 2007/0185084 A1 | 8/2007 | McKinney et al. |
| 2007/0270450 A1 | 11/2007 | Weber et al. |
| 2007/0275970 A1 | 11/2007 | Weber et al. |
| 2008/0027487 A1 | 1/2008 | Patel et al. |
| 2008/0058407 A1 | 3/2008 | Baron et al. |
| 2008/0110792 A1 | 5/2008 | McKinney et al. |
| 2008/0214592 A1 | 9/2008 | Cowley et al. |
| 2009/0018115 A1 | 1/2009 | Gadde et al. |
| 2009/0076108 A1 | 3/2009 | Gadde et al. |
| 2010/0166889 A1 | 7/2010 | Sanfilippo |
| 2010/0190793 A1 | 7/2010 | Weber et al. |
| 2011/0028505 A1 | 2/2011 | McKinney et al. |
| 2011/0098289 A1 | 4/2011 | Gadde et al. |
| 2011/0144145 A1 | 6/2011 | Tollefson |
| 2012/0010232 A1 | 1/2012 | Weber et al. |
| 2013/0177602 A1 | 7/2013 | McKinney et al. |
| 2013/0245056 A1 | 9/2013 | Flanagan |
| 2013/0252995 A1 | 9/2013 | Dunayevich et al. |
| 2014/0080857 A1 | 3/2014 | McKinney et al. |
| 2014/0364468 A1 | 12/2014 | Gadde et al. |
| 2015/0119417 A1 | 4/2015 | Tollefson |
| 2015/0141452 A1 | 5/2015 | Weber et al. |
| 2015/0164806 A1 | 6/2015 | McKinney et al. |
| 2015/0366860 A1 | 12/2015 | Klassen et al. |
| 2016/0143903 A1 | 5/2016 | Dunayevich et al. |
| 2016/0158221 A1 | 6/2016 | McKinney et al. |
| 2016/0158225 A1 | 6/2016 | McKinney et al. |
| 2016/0193152 A1 | 7/2016 | McKinney et al. |
| 2016/0310485 A1 | 10/2016 | Klassen et al. |
| 2016/0338965 A1 | 11/2016 | McKinney et al. |
| 2016/0354348 A1 | 12/2016 | McKinney et al. |
| 2017/0007598 A1 | 1/2017 | Weber et al. |
| 2017/0014404 A1 | 1/2017 | McKinney et al. |
| 2017/0020990 A1 | 1/2017 | Cowley et al. |
| 2017/0022380 A1 | 1/2017 | Nakagawa et al. |

FOREIGN PATENT DOCUMENTS

| | | |
|---|---|---|
| EP | 0 294 028 | 12/1988 |
| EP | 0 442 769 | 8/1991 |
| EP | 0 541 192 | 5/1993 |
| EP | 0 598 309 | 5/1994 |
| EP | 1 772 147 | 4/2007 |
| EP | 1 759 701 | 7/2007 |
| EP | 1 813 276 | 8/2007 |
| JP | 2003-502358 | 1/2003 |
| JP | 2003-509349 | 3/2003 |
| JP | 2006-232675 | 9/2006 |
| RU | 2197250 C2 | 1/2003 |
| RU | 2214241 | 10/2003 |
| RU | 2342195 C1 | 12/2008 |
| WO | WO 83/03197 | 9/1983 |
| WO | WO 90/13294 | 11/1990 |
| WO | WO 94/20100 | 9/1994 |
| WO | WO 96/09047 | 3/1996 |
| WO | WO 97/06786 | 2/1997 |
| WO | WO 97/06787 | 2/1997 |
| WO | WO 97/41873 | 11/1997 |
| WO | WO 98/00130 | 1/1998 |
| WO | WO 99/16375 | 4/1999 |
| WO | WO 99/37305 | 7/1999 |
| WO | WO 99/38504 | 8/1999 |
| WO | WO 00/050020 | 8/2000 |
| WO | WO 00/51546 | 9/2000 |
| WO | WO 00/61139 | 10/2000 |
| WO | WO 00/062757 | 10/2000 |
| WO | WO 00/76493 | 12/2000 |
| WO | WO 01/01973 | 1/2001 |
| WO | WO 01/26641 | 4/2001 |
| WO | WO 01/52833 | 7/2001 |
| WO | WO 01/52851 | 7/2001 |
| WO | WO 01/058447 | 8/2001 |
| WO | WO 01/58451 | 8/2001 |
| WO | WO 01/058451 | 8/2001 |
| WO | WO 01/62257 | 8/2001 |
| WO | WO 01/78725 | 10/2001 |
| WO | WO 01/85257 | 11/2001 |
| WO | WO 02/09694 | 2/2002 |
| WO | WO 02/24214 | 3/2002 |
| WO | WO 02/087590 | 11/2002 |
| WO | WO 03/013524 | 2/2003 |
| WO | WO 03/013525 | 2/2003 |
| WO | WO 03/013479 | 3/2003 |
| WO | WO 03/045355 | 6/2003 |
| WO | WO 03/092682 | 11/2003 |
| WO | WO 03/097051 | 11/2003 |
| WO | WO 04/002463 | 1/2004 |
| WO | WO 04/009015 | 1/2004 |
| WO | WO 04/024096 | 3/2004 |
| WO | WO 04/052289 | 6/2004 |
| WO | WO 04/054570 | 7/2004 |
| WO | WO 04/054571 | 7/2004 |
| WO | WO 04/060355 | 7/2004 |
| WO | WO 04/071423 | 8/2004 |
| WO | WO 04/091593 | 10/2004 |
| WO | WO 04/100956 | 11/2004 |
| WO | WO 04/100992 | 11/2004 |
| WO | WO 04/110368 | 12/2004 |
| WO | WO 04/110375 | 12/2004 |
| WO | WO 05/000217 | 1/2005 |
| WO | WO 05/077362 | 2/2005 |
| WO | WO 05/032555 | 4/2005 |
| WO | WO 05/049043 | 6/2005 |
| WO | WO 05/079773 | 9/2005 |
| WO | WO 05/089486 | 9/2005 |
| WO | WO 06/049941 | 5/2006 |
| WO | WO 06/052542 | 5/2006 |
| WO | WO 06/055854 | 5/2006 |
| WO | WO 06/088748 | 8/2006 |
| WO | WO 07/012064 | 1/2007 |
| WO | WO 07/024700 | 3/2007 |
| WO | WO 07/047351 | 4/2007 |
| WO | WO 07/85637 | 8/2007 |
| WO | WO 08/119978 | 10/2008 |
| WO | WO 11/119953 | 9/2011 |
| WO | WO 12/070043 | 5/2012 |
| WO | WO 13/184837 | 12/2013 |

OTHER PUBLICATIONS

Fruzzetti et al. "Effect of long-term naltrexone treatment on endocrine profile, clinical features, and insulin sensitivity in obese women with polycystic ovary syndrome," Fertility and Sterility vol. 77, No. 5, May 2002 (Year: 2002).*

(56) References Cited

OTHER PUBLICATIONS

Lustman et al. "Factors Influencing Glycemic Control in Type 2 Diabetes During Acute- and Maintenance-Phase Treatment of Major Depressive Disorder With Bupropion," Diabetes Care, vol. 30, No. 3, Mar. 2007. (Year: 2007).*
A multicenter, randomized, double-blind, placebo-controlled study assessing the occurrence of major adverse cardiovascular events (MACE) in overweight and obese subjects with cardiovascular risk factors receiving naltrexone SR/bupropion SR, Adis Clinical Trials Insight (Nov. 15, 2011), 5 pp.
Ackerman et al., 1998, Clinical characteristics of response to fluoxetine treatment of obsessive-compulsive disorder. Journal of Clinical Psychopharmacology, 18(3):185-192.
Adis Data Information BV, 2010, Naltrexone/Bupropion Contrave®; Naltrexone SR/Bupropion SR, Adis R&D Profile, 10(1):25-32.
Aigner et al., 2011, World Federation of Societies of Biological Psychiatry Guideline for the Pharmacological Treatment of Eating Disorders, The world Journal of Biological Psychiatry, 12:400-443.
Albaugh et al., 2005, Topiramate prevents the rapid weight gain and adiposity in a model of atypical antipsychotic drug-induced obesity, Fed. of American Soc. For Experimental Biology, 19(5, Suppl. S, Part 2):A1130.
Alger et al., Apr. 1991, Effect of a tricyclic antidepressant and opiate antagonist on binge-eating behavior in normoweight bulimic and obese, binge-eating subjects, The American Journal of Clinical Nutrition, 53(4):865-871.
Altman et al., 2005, Standard Deviations and Standard Errors, BMJ, 331:903.
Altomonte et al., 1988, Effect of fenfluramine on insulin/growth hormone ratio in obese subjects, Pharmacology, 36(2):106-111.
Anderson et al., 2002, Bupropion SR enhances weight loss: a 48-week double-blind, placebo-controlled trial, Obesity R., 10(7):633-641.
Appolinario et al., 2004, Pharmacological Approaches in the Treatment of Binge Eating Disorder, Current Drug Targets, 5:301-307.
Aronne et al., 2003, Weight gain in the treatment of mood disorders, J. Clin Psychiatry, 64(suppl 8).
Asconape, 2002, Some Common Issues in the Use of Antiepileptic Drugs, Seminars in Neurology; 22(1):27-39.
Astrup et al., Mar. 1991, Thermogenic Synergism Between Ephedrine and Caffeine in Healthy Volunteers: A Double-Blind, Placebo-Controlled Study, Metabolism, 40(3):323-329.
Atkinson et al. (Oct. 1985) Effects of long-term therapy with naltrexone on body weight in obesity, Clinical Pharmacology & Therapeutics, 38:419-422.
Atkinson, 2003, Clinical Guidelines on the identification, Evaluation, and pharmacologic treatment of obesity in Adults, Online, 07-25, URL:http://www.endotext.org.obesity/obesity15b/obesity15b.htm.
Atlantis et al., Oct. 6, 2009, Obesity and depression or anxiety, BMJ 2009;339:B3868.
Ayala (2000) Weight Loss Associated With the Administration of Zonisamide, AES Proceedings, Epilepsia 41 (Suppl. 7) :99—No. 2.041.
Ayala et al., Dec. 1-6, 2000, Weight loss associated with the administration of zonisamide, a compendium of posters and platform session for ZonegranTM and Diastat®, Annual Meeting 2000 of the American Epilepsy Society, Los Angeles, CA.
Bakris et al., 2002, Orlistat improves blood pressure and control in obese subjects with treated but inadequately controlled hypertension, Journal of Hypertension, 20(11):2257-2267.
Baldassano et al. (2006) Acute treatment of bipolar depression with adjunctive zonisamide: a retrospective chart review, Disorders 6:432-434.
Barr et al. 1993. The serotonin hypothesis of obsessive compulsive disorder. International Clinical Psychopharmacology, 8(2):79-82.
Bastani et al. 1991. Serotonin uptake and imipramine binding in the blood platelets of obsessive-compulsive disorder patients. Biol. Psychiatry, 30:131-139.

Bays et al., Aug. 1, 2007, Adiposopathy: treating pathogenic adipose tissue to reduce cardiovascular disease risk, Current Treatment Options in Cardiovascular Medicine, 9(4):259-271.
Beelen et al. (2001) Asymptomatic QTC prolongation associated with queitiapine fumarate overdose in a patient being treated with risperidone, Human & Experimental Toxicology 20:215-219.
Bengtsson, 1993, The consequences of growth hormone deficiency in adults, Acta Endocrinol. (Copenh.), 128(Suppl 2):2-5.
Benjamin et al. 1993. Naltrexone and fluoxetine in Prader-Willi syndrome. J. Am. Acad. Child Adolesc. Psychiatry, 32(4):870-873.
Bergeron et al. 2002. Sertraline and fluoxetine treatment of obsessive-compulsive disorder: Results of a double-blind, 6-month treatment study. Journal of Clinical Psychopharmacology, 22(2):148-154.
Berke et al. (Jul. 15, 2000) Medical Management of Obesity, American Academy of Family Physicians, 62(2):419-26 Abstract.
Billett et al. 1997. Obsessive compulsive disorder, response to serotonin reuptake inhibitors and the serotonin transporter gene. Molecular Psychiatry, 2:403-406.
Blanchard et al. (2003) Pancreatitis Treated with Didanosine and Tenofabir Disoproxil Fumarate Clinical Infectious Diseases, 37:57-62.
Bradley et al., Aug. 2002, Bupropion SR versus placebo: comparison of depressive symptoms and weight loss in obese patients with a history of major depression, International Journal of Obesity, 26(Suppl. 1):S156.
Broocks et al. 1998. Higher prevalence of obsessive-compulsive symptoms in patients with blepharospasm than in patients with hemifacial spasm. Am. J. Psychiatry, 155:555-557.
Brown et al., 2012, Current and emerging directions in the treatment of eating disorders, Substance Abuse: Research and Treatment, 6:33-61.
Brunk, Sep. 1, 2009, Significant weight loss shown with naltrexone/bupropion combo, Thoracic Surgery News, http://www.thoracicsurgerynews.com/?id=95937&tx_ttnews[tt_news]=86987&cHash=a97b7f3c0f6a8c6a3b3ca96df9a6b73f, 1 pp.
Bupropion (Oral Route), MayoClinic.com, 19 pp., 2009.
Calabrese et al. (Sep. 2000) Letters to the Editors, Lamotrigine and Clozapine for Bipolar Disorder, American J. of Psychiatry, 157:1523.
Campana et al., Jan. 2005, P.6.034 Naltrexone and cravings: does it work with eating disorders?, European Neuropsychopharmacology, 15:S283.
Carlsen et al. (Jan. 1998) Evidence for dissociation of insulin-and weight-reducing effects of metformin in non-diabetic male patients with coronary heart disease, Diabetes Research and Clinical Practice Amsterdam, 39(1):47-54.
Carpenter et al. (Jan. 1, 1999) Mirtazapine Augmentation in the Treatment of Refractory Depression, J Clin Psychiatry, 60:1.
Carrion, 1995. Naltrexone for the treatment of trichotillomania: A case report. J. Clin. Psychopharmacol., 15(6):444-445.
Carroll (2003) Medicinal Chemistry Division Award Address: Monoamine Transporters and Opioid Receptors. Targets for Addiction Therapy, J. Med. Chem; 46(10):1775-1794.
Carson et al., May 1996, Pilot study of the use of naltrexone to treat the severe pruritis of cholestatic liver disease, Amer. J. Gastroenterology, 91(5):1022-1023.
Carter et al. 2003. Pharmacologic treatment of binge-eating disorder, The International Journal of Eating Disorders, 34(Suppl):S74-S88.
Carter et al. 2003. Pharmacologic treatment of binge-eating disorder. Primary Psychiatry, 10(10)31-36.
Casado et al., Apr. 2003, Sibutramine decreases body weight gain and increases energy expenditure in obese Zucker rats without changes in NPY and orexins, Nutr Neurosci, 6(2):103-111 (abstract).
Cash et al. (2000) Attitudes about antidepressants: Influence of information about weight-related side effects, Perceptual and Motor Skills, 90:453-456.
Casner et al. 1996. Naltrexone and self-injurious behavior: A retrospective population study. Journal of Clinical Psychopharmacology, 16(5):389-394.
Chakraborty et al., 2010, Management of anorexia and bulimia nervosa: an evidence-based review, Indian J Psychiatry, 52:174-186.

(56) References Cited

OTHER PUBLICATIONS

Chen et al. (Jan. 2004) Synergistic Effects of Cannabinoid inverse agonist AM251 and opioid antagonist nalmefene on food intake, Brain Res, 999:22-230.
Chen et al., 2005, Combination treatment of clozapine and (No Suggestions) in resistant rapid-cycling bipolar disorder, Clin. Neuropharmacol. 28(3):136-138.
Chen et al., Jun. 2003, Nonketotic hyperosmolar syndrome from olanzapine, lithium, and valproic acid cotreatment, Annals of Pharmacotherapy, 37(6):919-920.
Chengappa et al. (2002) Changes in body Weight and Body mass index among psychiatric patients receiving lithium, valproate, or topiramate: an open-label, nonrandomized chart review, Clinical Therapeutics, 24(10):1576-1584.
Ching, Mar. 1980, Influence of diphenylhydantoin upon oral glucose tolerance test in obesity, Chinese Medical Journal, 27(1):432-439.
Chouinard et al. 1996. Potentiation of fluoxetine by aminoglutethimide, an adrenal steroid suppressant, in obsessive-compulsive disorder resistant to SSRIs: A case report. Prog. Neuro-Psychopharmacol. & Biol. Psychiat., 20:1067-1079.
Clapham et al. (2001) Anti-obesity drugs: a critical review of current therapies and future opportunities. Pharmacology & Therapeutics. 89:81-121.
Clark et al., 2003, Diabetes mellitus associated with atypical antipsychotic medications, Diabetes Technology & Therapeutics, 5(4):669-683.
Cleveland Clinic Press Release: "Clinical Trial Testing Safety of Obesity Drug Contrave Halted; 50 Percent Interim Data Released By the Study's Executive Committee", May 12, 2015, retrieved from http://my.clevelandclinic.org/about-cleveland-clinic/newsroom/releases-videos-newsletters/2015-5-12-clinical-trial-testing-safety-of-obesity-drug-contrave-halted.
Clinical Trial: Drug Treatment for Depressed Alcoholics (Naltrexone/Fluoxetine). (n.d.) Retrieved Jun. 28, 2007, from http://www.clinicaltrials.gov/ct/show/NCT00006204;jsessionid+FED6D0856E098BC0B1940E464179B71B?order=28.
Clinical Trials.gov, A Multicenter, randomized, double-blind, placebo-controlled study assessing the occurrence of major adverse cardiovascular events (MACE) such as cardiovascular death, non-fatal myocardial infarction, and non-fatal stroke in overweight and obese subjects who are at a higher risk of having these events because they have diabetes and/or other cardiovascular risk factors, NTC01601704, May 7, 2013, 4 pp.
Clinical Trials.gov, Jul. 13, 2009, An open-label study assessing the safety and efficacy of naltrexone sustained release (SR)/bupropion sustained release (SR) in overweight or obese subjects with major depression, 2 pp.
ClinicalTrials.gov archive, Apr. 21, 2008, A phase 3 study comparing the safety and efficacy of naltrexone sr/bupropion sr and placebo in obese subjects with type 2 diabetes mellitus, 3 pp.
ClinicalTrials.gov archive, May 2012, Cardiovascular outcomes study of Naltrexone SR/Bupropion SR in overweight and obese subjects with cardiovascular risk factors (the light study), 4 pp.
ClinicalTrials.gov, Apr. 3, 2007, A safety and efficacy study of naltrexone sr/bupropion sr and placebo in overweight and obese subjects participating in an intensive behavior modification program, NCT00456521, 5 pp.
Colosimo, et al. 1999. Motor fluctuations in Parkinson's disease: Pathophysiology and treatment. European Journal of Neurology, 6:1-21.
Cone et al. (2001) The arcuate nucleus as a conduit for diverse signals relevant to energy homeostasis, Int'l Journal of Obesity, 25(5):S63-S67.
Croft et al. (Apr. 2002) Effect on body weight of bupropion sustained-release in patients with major depression treated for 52 weeks, Clinical Therapeutics 24(4):662-672.
Cunningham, May 1963, Diethylpropion in the treatment of obesity, The Journal of the College of General Practitioner, 6(2):347-349.

Cuparencu et al., 1993, Effects of some benzodiazepines on glycemia in albino rats, Romanian Journal of Physiology, 30(1-2):7-15 (abstract).
Das et al., 2003, Controlled-release of oral dosage forms, Formulation, Fill & Finish, pp. 10-16.
De Boer et al., 1995, Clinical aspects of growth hormone deficiency in adults, Endocrine Reviews, 16(1):63-86.
Dechant et al., 1991, Paroxetine: a review of its pharmacodynamic and pharmacokinetic properties, and therapeutic potential in depressive illness, Drugs, 41:225-253.
Defendant Actavis Laboratories FL, Inc.'s Initial Invalidity Contentions for U.S. Pat. No. 9,125,868, in *Takeda Pharmaceutical Company Limited et al.*, Plaintiffs, v. *Actavis Laboratories FL, Inc.*, Defendant, C.A. No. 15-451-RGA, US District Court for the District of Delaware, dated Jul. 25, 2016, 48 pp.
Dembowski et al. (2003) Successful Antimanic Treatment and Mood Stabilization with Lamotrigine, Clozapine, and Valproate in a Bipolar Patient after Lithium-induced Cerebellar Deterioration, Letter Pharmacopsychiatry, 36:83-86.
Deshmukh et al. (Jul. 2003) Managing weight gain as a side effect of antidepressant therapy, Cleveland Clinic Journal of Medicine, 70(7):614-623.
DeSimone et al. (2005) Carbonic anhydrase inhibitors. Zonisamide is an effective inhibitor of the cytosolic isozyme II and mitochondrial isozyme V: Solution and x-ray crystallographic studies, Bioorganic & Medicinal Chemistry Letters, 15:2315-2320.
Devlin et al. (2000) Open treatment of overweight binge eaters with phentermine and fluoxetine as an adjunct to cognitive-behavioral therapy. Int. J. Eating Disord; 28:325-332.
Drugs.com, Sep. 20, 2011, Orexigen and FDA identify a clear and feasible path to approval for contrave, http://www.drugs.com/nda/contrave_110920.html, 4 pp.
Durgin et al., 2005, Pharmaceutical Practice for Technicians, 3rd Edition, Thomson Delmar Learning, p. 174.
Dursun et al. (2001) Accelerated Weight Loss After Treating Refractory Depression with Fluoxetine Plus Topiramate: Possible Mechanism of Action, Canadian Journal of Psychiatry, 46(3):287-288.
Dursun et al. (2001) Augmenting Antipsychotic treatment with Lamotrigine or topiramate in patients with treatment-resistant Schizophrenia: a naturalistic case-series outcome study Journal of Psychopharmacology 15(4):297-301.
Dursun et al. (2001) Psychopharmacology for the Clinician Psychopharmacologie Pratiqu, Journal of Psychiatry Neuroscience, 26(2):168.
Dursun et al. (Oct. 1999) Clozapine Plus Lamotrigine in Treatment-Resistant Schizophrenia, Arch Gen Psychiatry, 56:950-951.
Dwyer et al., 2002, Psychoactive drugs affect glucose transport and the regulation of glucose metabolism, International Review of Neurobiology, 51:503-530.
Eckel et al., Apr. 16, 2005, The metabolic syndrome, The Lancet 365:1415-1428.
Eid et al., 2005, Effective treatment of polycystic ovarian syndrome with roux-en-y gastric bypass, Surgery for Obesity and Related Diseases, 1:77-80.
El-Haschimi et al. 2000. Two defects contribute to hypothalamic leptin resistance in mice with diet-induced obesity. The Journal of Clinical Investigation, 105(12):1827-1832.
Erez et al., 1982, Narcotic antagonistic potency of bivalent ligands which contain ß-naltrexamine. Evidence for bridging between proximal recognition sites, J. Med. Chem., 25:847-849.
Erfurth et al., Mar. 2002, Bupropion as add-on strategy in difficult-to-treat bipolar depressive patients, Neurophsychobiology, 45(Supplement 1):33-36.
Erzegovesi et al. 2001. Clinical predictors of drug response in obsessive-compulsive disorder. Journal of Clinical Psychopharmacology, 21(5):488-492.
Esposito-Avella et al. (Jan. 1973) Studies on the protective effect of diphenylhyndantoin against alioxan diabetes in mice, Proceedings of the Society for Experimental Biology & Medicine, 142(1):82-85.
Ettmayer et al, May 6, 2004, Lessons learned from marketed and investigational prodrugs, J. Med. Chem, 47(10):2393-2404.
Faught et al. (2001) Randomized Controlled Trial of Zonisamide for the Treatment of Refractory Partial-Onset Seizures., Neurology; 57(10):1774-1779.

(56) References Cited

OTHER PUBLICATIONS

Fava, 2000, Weight Gain and Antidepressants. J Clin Psychiatry; 61 (suppl 11):37-41.
Ferre et al. (1996) Correction of diabetic alterations by glucokinase. Proc. Natl. Acad. Sci. USA, 93:7225-7230.
Ferre et al. (1996) Evidence from transgenic mice that glucokinase is rate limiting for glucose utilization in the liver, The FASEB Journal, 10:1213-1218.
Fingl et al., The Pharmacological Basis of Therapeutics. Chapter 1: General Principles, pp. 1-46 (1975).
Fontela et al., Mar. 1986, Blocking effect of naloxone, dihydroergotamine and adrenalectomy in lithium-induced hyperglycaemia and glucose intolerance in the rat, Acta Endocrinologica, 111(3):342-348 (abstract).
Fujioka et al., Jan. 1987, Contribution of intra-abdominal fat accumulation to the impairment of glucose and lipid metabolism in human obesity, Metabolism, 36(1):54-59.
Fukagawa et al. (Nov. 2001) Monoaminergic anorectic agents, Nippon Yikurigaku Zasshi, 118(5):303-8, 2001 Abstract.
Fulghesu et al. (Aug. 1993) Long-term naltrexone treatment reduces the exaggerated insulin secretion in patients with polycystic ovary disease, Obstetrics & Gynecology, 82(2):191-197.
Fuller et al. (1989) Fluoxetine: A Serotonergic Appetite Suppressant Drug, Drug Development Research, 17(1):1-15.
Gadde et al., "Zonisamide in Obesity: A 16-Week Randomized Trial", No. NR473, New Research, American Psychiatric Association 2002 Annual Meeting, May 18-23, 2002, Philadelphia, Pennsylvania (abstract).
Gadde et al, Randomized Trial of Weight Loss Efficacy of Zonisamide, No. 304, 26(Suppl. 1), Journal of the International Association for the Study of Obesity, Ninth International Congress on Obesity, Sao Paolo, Brazil, Aug. 24-29, 2002.
Gadde et al. "Bupropion for Weight Loss: An Investigation of Efficacy and Tolerability in Overweight and Obese Women" Obesity Research 9(9):544-551 (2001).
Gadde et al., "Zonisamide for Weight Loss in Obese Adults—A Randomized Controlled Trial" JAMA 289 (14): 1820-1825 (2003).
Gadde et al., 2002, Randomized controlled trial of zonisamide for treating obesity, Epilepsia 43 Suppl. 7:218 (abstract).
Gadde et al., 2003, Zonisamide enhances weight loss in patients with obesity. Inpharma, 1383(84):9.
Gadde et al., May 1999, Bupropion Sustained Release in Obesity: A Randomized Double-Blind, Placebo-Controlled Study, No. NR634, New Research Program & Abstracts, American Psychiatric Association, 1999 Annual Meeting, The Clinician, Washington, D.C.
Gadde et al., Sep. 1999, A randomized double-blind placebo-controlled study of bupropion sustained release in obesity, European Neuropsychopharmacology, 9(5):366.
Gatley et al.,1996, 123I-labeled AM251: a radioiodinated ligand which binds in vivo to mouse brain cannabinoid CB1 receptors. European Journal of Pharmacology; 307:331-338.
Gehlert et al. (Oct. 1998) The Selective Norepinephrine Reuptake Inhibitor, LY368975, Reduces Food Consumption in Animal Models of Feeding, J. Pharmacology and Experimental Therapeutics, 87(1):122-7 Abstract.
Gerich et al. (1972) In vitro inhibition of pancreative glucagon secretion by diphenylhydantoin, Journal of Clinical Endocrinology and Metabolism 35(6):823-824.
Gerra et al. 1995. Hostility in heroin abusers subtypes: Fluoxetine and naltrexone treatment. Prog. Neuro-Psychopharmacol. & Biol. Psychiat., 19:1225-1237.
Gerra et al., Sep. 30, 2006, Effects of olanzapine on aggressiveness in heroin dependent patients, Progress in Neuro-Psychopharmacology & Biological Psychiatry, 30(7):1291-1298.
Ghisoli et al., 1980, Effects of interaction between 2-Br-$\alpha$-ergocryptine (CB 154) and naloxone on the control of insulin secretion in normal man, Boll. Soc. Ital. Biol. Sper., 56(12):1215-1221.
Ginsberg et al. (2000) Effects of Mood Stabilizers on Weight, Primary Psychiatry 7(5):49-58.
Givens et al. (1987) Reduction of hyperinsulinemia and insulin resistance by opiate receptor blockade in the polycystic ovary syndrome with acanthosis nigricans, Journal of Clinical Endocrinology and Metabolism, 64(2):377-382.
Glass et al., 1999, Opioids and food intake: distributed functional neural pathways?, Neuropeptides, 33(5):360-368.
Glod et al., Jul.-Sep. 2003, Open trial of bupropion sr in adolescent major depression, J Child Adolesc Psychiatr Nurs, 16(3):123-130.
Goldstein et al. (Mar. 1994) Fluoxetine: a randomized clinical trial in the treatment of obesity, International Journal of Obesity and Related Metabolic Disorders, 17(3):129-135, CAS accession #9424430.
Goodman & Gillman's, The Pharmacological Basis of Therapeutics, 10th Ed., Edited by J. Hardman and L. Limbird, 2001, p. 6.
Goodman et al. 1989. The Yale-Brown obsessive compulsive scale. Arch. Gen. Psychiatry, 46:1006-1011.
Goodpaster et al., Feb. 2003, Association between regional adipose tissue distribution and both type 2 diabetes and impaired glucose tolerance in elderly men and women, Diabetes Care, 26(2):372-379.
Gordon et al. (Jun. 1999) Mood Stabilization and Weight Loss with Topiramate American Journal of Psychiatry, American Psychiatric Association, Washington D.C., 156(6):968-969.
Gormally et al., 1982, The assessment of binge eating severity among obese persons, Addict Behav, 7(1):47-55.
Grady (Mar. 15, 2003) Quest for Weight-Loss Drug Takes an Unusual Turn, The New York Times—Health, www.nytimes.com, 3 pp.
Grant et al. 2004. Impulse control disorders: Clinical characteristics and pharmacological management. Annals of Clinical Psychiatry, 16:27-34.
Grant et al. 2004. Pharmacotherapy outcome in older pathological gamblers: A preliminary investigation. Journal of Geriatric Psychiatry and Neurology, 17(1):9-12.
Grant et al. 2006. Compulsive aspects of impulse-control disorders. Psychiatr. Clin. North Am., 29(2):539-x.
Greenberg et al. 1998. Delayed obsessive-compulsive disorder symptom exacerbation after a single dose of a serotonin antagonist in fluoxetine-treated but not untreated patients. Psychopharmacology, 140:434-444.
Greenway et al. (2002) A Long-acting Leptin Analog does not Enhance Fat, Visceral Fat, or Weight Loss When Combined with Caffeine Ephedrine in Obese Subjects, International Journal of Obesity, S136.
Greenway et al. (Jul. 1999) Double-Blind, Randomized, Placebo-Controlled Clinical Trials with Non-prescription Medications for the Treatment of Obesity, Obesity Research, 7(4):370-78.
Greenway et al., Dec. 2009, Comparison of combined bupropion and naltrexone therapy for obesity with monotherapy and placebo, J. Clin Endocrinol Metab, 94(12):4898-4906.
Greenway et al., Jan. 2009, Rational design of a combination medication for the treatment of obesity, Obesity, 17(1):30-39.
Greenway et al., Jun. 2006, Bupropion and naltrexone for the treatment of obesity, Diabetes: Abstract Book: 66th Scientific Sessions, 55(Supplement 1):A395.
Greenway et al., Jun. 2006, Bupropion and naltrexone for the treatment of obesity, poster, 1 pg.
Greenway et al., Oct. 22, 2010, Effect of naltrexone plus bupropion on weight loss in overweight and obese adults (COR-I): a multicentre, randomized, double-blind, placebo-controlled, phase 3 trial, Lancet, 376:595-605.
Greist et al. (Apr. 1995) Double-blind Parallel Comparison of Three Dosages of Sertraline and Placebo in Outpatients With Obsessive-compulsive Disorder, Arch Gen Psychiatry, 52:289-295.
Grundy et al., 2005, Diagnosis and management of the metabolic syndrome, Circulation, 112:2735-2752.
Grunenthal, Neo-Eunomin Gebrauschsinformation, Neunomin Prescription Information, Feb. 2004, pp. 1-2.
Guidance for Industry Estimating the Maximum Safe Starting Dose in Initial Clinical Trials for Therapeutics in Adult Healthy Volunteers, U.S. Department of Health and Human Services, U.S. Food and Drug Administration Center for Drug Evaluation and Research (CDER), Pharmacology and Toxicology, Jul. 2005.

(56) References Cited

OTHER PUBLICATIONS

Hagan et al., Dec. 1997, Combined naloxone and fluoxetine on deprivation-induced binge eating of palatable foods in rats, Pharmacol Biochem Behav, 58(4):1103-1107.

Hahn et al. (1985) Irreversible opiate agonists and antagonists. III. Phenylhydrazone derivatives of naloxone and oxymorphone. J. Pharm. Exper. Therapeutics; 235:846-850.

Halford et al., May 2010, Pharmacological management of appetite expression in obesity, Nature Reviews Endocrinology, 6(5):255-269.

Halpern et al., Jul. 27, 2010, Combinations of drugs in the treatment of obesity, Pharmaceuticals, 3:2398-2415.

Hamidi et al. 2007. Naltrexone in obsessive-compulsive disorder: An open-label trial. Iranian Journal of Psychiatry and Behavioral Sciences, 1(1):16-21.

Harrison's Principles of Internal Medicine, Braunwald et al., The epilepsies and convulsive disorders, Eleventh Edition, McGraw-Hill Book Company, pp. 1921-1930 (1987).

Hashiguti et al. (1993) Simultaneous determination of in vivo hydroxylation of tyrosine and tryptophan in rat striatum by microdialysis—HPLC: relationship between dopamine and serotonin biosynthesis; Journal of Neural Transmission, 93:213-223.

Hausenloy, 2009, Contrave™: Novel treatment for obesity, Clinical Lipidology, 4(3):279-285.

Herper, "A Top Cardiologist Says A Diet Drug Maker Misled Patients And Investors", Forbes, May 12, 2015, retrieved from http://www.forbes.com/sites/matthewherper/2015/05/12/a-top-cardiologist-says-a-diet-drug-maker-misled-patients-and-investors/#.

Herper, "Heart Benefit For Orexigen Drug Nearly Vanishes with New Data", Forbes, May 12, 2015, retrieved from http://www.forbes.com/sites/matthewherper/2015/05/12/heart-benefit-for-orexigen-drug-nearly-vanishes-with-new-data/.

Herper, Mar. 5, 2015, Top FDA Official Says Orexigen Study Result 'Unreliable,' Misleading, http://www/forbes.com/sites/matthewherper/, 4 pp.

Hollander et al. 1991. Effects of chronic fluoxetine treatment on behavioral and neuroendocrine responses to meta-chlorophenylpiperazine in obsessive-compulsive disorder. Psychiatry Research, 36:1-17.

Hollander et al., Oct. 21, 2013, Effects of naltrexone sustained-release/bupropion sustained release combination therapy on body weight and glycemic parameters in overweight and obese patents with type 2 diabetes, Diabetes Care, 36(12):4022-4029.

Horne et al., Jul. 1988, Treatment of bulimia with bupropion: a multicenter controlled trial, The Journal of Clinical Psychiatry, 49(7):262-266.

Hussey et al., 2002, Synthesis of a ß-estradiol-biotin chimera that potently heterodimerizes estrogen receptor and streptavidin proteins in a yeast three-hybrid system, J. Am. Chem. Soc., 125:3692-3693.

Husten, Mar. 3, 2015, Orexigen Released Interim Data Without Approval of Trial Leaders, http://ww/forbes.com/sites/harryhusten, 6 pp.

Insulin Resistance and Pre-diabetes, http://diabetes.niddk.hih.gov/DM/pubs/insulineresistance/, NIH Publication No. 09/4893, Oct. 2008, 9 pp.

Ioannides-Demos et al., 2005, Pharmacotherapy for obesity, Drugs, 65(10):1391-1418.

Islam et al., 1994, Naltrexone, Serotonin Receptor Subtype Antagonists, and Carbohydrate Intake in Rats, Pharmacology Biochemistry and Behavior, 48(1):193-201.

Jain et al. (Oct. 2002) Bupropion SR vs. Placebo for Weight Loss in Obese Patients with Depressive Symptoms, Obesity Research, 10:1049-1056.

Jallon et al. (2001) Bodyweight gain and anticonvulsants: a comparative review. Drug Safety; 24(13):969-978.

Janssen et al., 1999, Effects of sex on the change in visceral, subcutaneous adipose tissue and skeletal muscle in response to weight loss, International Journal of Obesity, 23, pp. 1035-1046.

Japanese Journal of Clinical Psychiatry (1987 16(1):123-132), and English-language version of Japanese Office Action citing the same (dated Oct. 28, 2008).

Johannsson et al., 1997, Growth hormone treatment of abdominally obese men reduces abdominal fat mass, improves glucose and lipoprotein metabolism, and reduces diastolic blood pressure, J. Clin. Endocrin. and Metab., 82(3):727-734.

Johnson et al., Oct. 14, 2010, Food effects on the pharmacokinetics of morphine sulfate and naltrexone hydrochloride extended release capsules, Advances in Therapy, 27(11):846-858.

Johnston et al., 2002, Pharmacokinetic optimization of sustained-release bupropion for smoking cessation, Drugs, 62(Suppl. 2):11-24.

Jonas et al.., 1986, Treatment of binge-eating an open-study of naltrexone, Society for Neuroscience Abstracts, 12(1):595.

Jones et al., 2003, Effect of naltrexone on food intake and body weight in Syrian hamsters depends on metabolic status, Physiology & Behavior 28:67-72.

Kanba et al. (1994) The first open study of zonisamide, a novel anticonvulsant, shows efficacy in mania. Progress in Neuro-Psychopharmacology and Biological Psychiatry; 18(4):707-715.

Katsiki et al., Jun. 1, 2011, Naltrexone sustained-release (SR) + bupropion SR combination therapy for the treatment of obesity: 'a new kid on the block'?, Annals of Medicine, 43(4):249-258.

Kelley et al., 2000, A pharmacological analysis of the substrates underlying conditioned feeding induced by repeated opioid stimulation of the nucleus accumbens, Neuropsychopharmacology, 23(4):455-467.

Kelly et al., 2006, Adjunct divalproex or lithium to clozapine in treatment-resistant schizophrenia, Psychiatric Quarterly, 77(1):81-94.

Kennett et al., Nov. 2010, New approaches to the pharmacological treatment of obesity: can they break through the efficacy barrier?, Pharmacology Biochemistry and Behavior, 97(1):63-83.

Khaylis et al., Nov. 2010, A review of efficacious technology-based weight-loss interventions: five key components, Telemedicine and e-Health, 16(9):931-938.

Kim et al. 1990. Open fixed dose trial of fluoxetine in the treatment of obsessive compulsive disorder. Drug Development Research, 19:315-319.

Kimura et al., 1992, Pharmacokinetic interaction of zonisamide in rats: effects of other antiepileptics on zonisamide, J. Pharmacobio-Dyn. 15:631-639.

Kiptoo et al. (2006) Enhancement of Transdermal delivery or 6-B-naltrexol via a codrug linked to hydroxybupropion, Journal of Controlled Release 113:137-145.

Kirkham et al. (2001) Synergistic effects of opioid and cannabinoid antagonists on food intake. Psychopharmacology; 153:267-270.

Kirov et al. (2003) Add-on topiramate reduces weight in overweight patients with affective disorders: a clinical case. BMC Psychiatry, 5:19, 8 pp.

Kivimaki et al., Common mental disorder and obesity—insight from four repeat measures over 19 years: prospective Whitehall II cohort study, BMJ 2009; 339:b3765.

Klein et al., Jun. 1, 2009, Naltrexone plus bupropion combination causes significant weight loss without worsening psychiatric symptoms, Diabetes, 58(Suppl. 1):A444, Abstract 1739-P.

Klok et al., 2002, Cholesteryl-(I-lactic acid)n building blocks for self-assembling biomaterials, Macromolecules, 35:746-759.

Kolb et al. (1985) Synthesis and Pharmacological Characterization of Fluorescent Opioid Receptor Probes. A. Pharmaceutical Res, 2(6):266-271.

Korner et al. (2003) The emerging science of body weight regulation and its impact on obesity treatment, J. Clin. Invest. 111(5):565-570.

Kossard, et al. 2006. Defining urticarial dermatitis: A subset of dermal hypersensitivity reaction pattern. Arch. Dermatol., 142:29-34.

Krauss et al. 1997. Tics secondary to craniocerebral trauma, Movement Disorders, 12(5):776-782.

Kristeller et al., Jan. 12, 1999, An exploratory study of a meditation-based intervention for binge eating disorder, J. Health Psychol, 4(3):357-363.

(56) References Cited

OTHER PUBLICATIONS

Kruger, 2000, Psychopharmacotherapy of anorexia nervosa, bulimia nervosa and binge-eating disorder, J. Psychiatry Neurosci, 25(5):497-508.
Krupitsky et al. 2006. Naltrexone with or without fluoxetine for preventing relapse to heroin addiction in St. Petersburg, Russia. Journal of Substance Abuse Treatment, 31:319-328.
Kuk et al., 2006, Visceral fat is an independent predictor of all-cause mortality in men, Obesity, 14(2):336-341.
Kushner et al. (Mar. 2002) Obesity pharmacology: past, present, and future, Current Opinion in Gastroenterology, pp. 213-220.
Laessle et al., May 1997, A comparison of resting metabolic rate, self-rated food intake, growth hormone, and insulin levels in obese and nonobese preadolescents, Physiol. Behav., 61(5):725-729.
Landabaso et al. 1998. A randomized trial of adding fluoxetine to a naltrexone treatment programme for heroin addicts. Addiction, 93(5):739-744.
Le Bourdonnec et al., 2002, Reporter affinity labels: an o-phthalaldehyde derivative of β-naltrexamine as a fluorogenic ligand for opioid receptors, J. Med. Chem., 43(13):2489-2492.
Leppik (Dec. 2004) Zonisamide: chemistry, mechanism of action, and pharmacokinetics, Seizure, 13(Suppl 1):S5-9; discussion S10.
Leppik et al. (1993) Efficacy and safety of zonisamide: results of a multicenter study. Epilepsy Research; 14:165-173.
Lesch et al. 1991. Long-term fluoxetine treatment decreases 5-HT1A receptor responsivity in obsessive-compulsive disorder. Psychopharmacology, 105:415-420.
Lessig et al. (Dec. 2001) Topiramate for Reversing Atypical Antipsychotic Weight Gain, J. Am. Child Adolesc. Psychiatry 40(12):1364.
Levy et al. (Nov. 2002) Topiramate Produced Weight Loss Following Olanzapine-Induced Weight Gain in Schizophrenia, J. Clin. Psychiatry, 63(11):1045.
Levy et al. 1985. Utility of free level monitoring of antiepileptic drugs. Epilepsia, 26(3):199-205.
Lin et al. 2000. Development of high fat diet-induced obesity and leptin resistance in C57B1/6J mice. International Journal of Obesity, 24:639-646.
López-Ibor, Jr. et al. 1996. Double-blind comparison of fluoxetine versus clomipramine in the treatment of obsessive compulsive disorder. European Neuropsychopharmacology, 6:111-118.
Lowry, Feb. 2008, Study: bupropion-naltrexone combo best for weight loss, Clinical Psychiatric News, 1 pp.
Ludman et al., "Does depression reduce the effectiveness of behavioral weight loss treatment?" Behav Med. 2010; 35(4):126-134 (abstract).
Luppino et al., Mar. 2010, Overweight, obesity, and depression: a systematic review and meta-analysis of longitudinal studies, Arch Gen Psychiatry, 67(3):220-229.
Malcolm et al. (Jun. 1985) A Controlled Trial of Naltrexone in Obese Humans, International Journal of Obesity, 9:347-353.
Malhotra et al. (2002) Medical Management of Obesity Associated With Mental Disorders, Journal of Clinical Psychiatry, 63(suppl 4):24-32.
Marrazzi et al., Feb. 1995, Binge eating disorder: response to naltrexone, International Journal of Obesity, 19(2):143-145.
Matsuura (2000) Indication for Anterior Temporal Lobectomy in Patients with Temporal Lobe Epilepsy and Psychopathology, Epilepsia, 41(Suppl. 9):39-42.
McDougle et al. (Aug. 2000) A double-blind, placebo-controlled study of risperidone addition in serotonin reuptake inhibitor-refractory obsessive-compulsive disorder, Archive of General Psychiatry, 57(8):794-801.
McElroy et al. (2000) Pharmacologic agents for the treatment of acute bipolar mania, Biological Psychiatry, 48(6):539-557.
McElroy et al. (2004) Zonisamide in the Treatment of Binge-Eating Disorder: An Open-Label, Prospective Trial, J. Clin. Psychiatry, 65(1):50-56.
McElroy et al. (2004) Zonisamide is effective in the treatment of binge-eating disorder. Inpharma; 1428:10.
McElroy et al., Jun. 1, 2010, An open-label study evaluating the naltrexone SR/bupropion SR combination therapy in overweight or obese subjects with major depression, Diabetes, 59(Suppl. 1):A483.
McElroy et al., Jun. 2013, Naltrexone/bupropion combination therapy in overweight or obese patients with major depressive disorder: results of a pilot study, Prim Care Companion CNS Disord, 15(3), 17 pp.
McElroy et al., May 7, 2012, Pharmacological management of binge-eating disorder: current and emerging treatment options, Therapeutics and Clinical Risk Management, 8:219-241.
McElroy et al., Nov. 2010, Reduced depressive symptoms and weight loss in depressed overweight/obese subjects completing 24 weeks of open label therapy with naltrexone sr/bupropion sr, 18(Supp 2):S152.
McLaughlin et al. (2003) The cannabinoid CB1 antagonists SR 141716A and AM 251 suppress food intake and food-reinforced behavior in a variety of tasks in rats. Behavioral Pharmacology; 14:583:588.
McLaughlin et al., 1983, Nalmefene decreases meal size, food and water intake and weight gain in Zucker rats, Pharmacology Biochemistry and Behavior, 19(2):235-240 (abstract).
Melander, Oct. 1978, Influence of food on the bioavailability of drugs, Clinical Pharmacokinetics, 3(5):337-351.
Meyer et al., Sep. 1984, Bioequivalence, dose-proportionality, and pharmacokinetics of naltrexone after oral administration, J. Clin. Psychiatry, 45(9)(Sec. 2):15-19.
Meyer, Dec. 2008, Alleviation of both binge eating and sexual dysfunction with naltrexone, Journal of Clinical Psychopharmacology, 28(6):722-723.
Michelson et al. (Nov. 2001) Atomexetine in the Treatment of Children and Adolescents with Attention Deficit/Hyperactivity Disorder: A Randomized, Placebo-Controlled, Dose-Response Study, Pediatrics,108(5):E83 Abstract.
Midha et al., May 2005, Exposure measures applied to the bioequivalence of two sustained release formulations of bupropion, International Journal of Clinical Pharmacology and Therapeutics, 43(5):244-254.
Milano et al., May-Jun. 2005, Treatment of bulimia nervosa with fluvoxamine: a randomized controlled trial, Advances in Therapy, 22(3):278-283.
Millet et al. 1999. Obsessive-compulsive disorder: Evaluation of clinical and biological circadian parameters during fluoxetine treatment. Psychopharmacology, 146:268-274.
Mitchell et al. (1987) High-Dose Naltrexone Therapy and Dietary Counseling for Obesity, Biological Psychiatry, 22:35-42.
Miyazaki, 2005, Adiposity and Drug Treatment, Resident Notes, 7(4):499-502.
Monteleone et al. 1995. Plasma melatonin and cortisol circadian patterns in patients with obsessive-compulsive disorder before and after fluoxetine treatment. Psychoneuroendocrinology, 20(7):763-770.
Morris, III (Dec. 3, 2000) The Effect of Zonisamide Administration on Patient Weight, A Scientific Exhibit at the American Epilepsy Society Annual Meeting, Los Angeles, California.
Mukherjee, "Update: Takeda threatens to break off Orexigen collab after Contrave data drama", BioPharmaDive, May 13, 2015, retrieved from http://www.biopharmadive.com/news/update-takeda-threatens-to-break-off-orexigen-collab-after-contrave-data-d/396940/.
Must et al. (Oct. 27, 1999) The disease burden associated with overweight and obesity, JAMA, 282(16):1523-1529.
Najim et al., Dec. 1, 1993, Role of endorphins in benzodiazepine-induced hyperglycaemia in mice, Pharmacology Biochemistry and Behavior, 46(4):995-997.
Naltrexone (Oral Route), MayoClinic.com, 11 pp., 2009.
Nash et al., Jul. 1, 2004, Anxiety disorders, Medicine, 32(7):17-21.
National Institutes of Health, Apr. 18, 2008, Efficacy and safety study of combination therapy to treat uncomplicated obesity, http://clinicaltrials.gov/show/NCT00364871, 5 pp.
Navarro et al. (Jun. 2001) Topiramate for Clozapine-Induced Seizures, Am. J. Psychiatry, 158(6):968-969.
NDA 20-711, Approval Letter of Application No. NDA 20-711, Department of Health and Human Services, May 14, 1997, 4 pp.

(56) References Cited

OTHER PUBLICATIONS

NDA 20-789/S-005 Zonegran (zonisamide) Capsules 100 mg, FDA Approved Labeling Text dated Oct. 7, 2002, 2 pp.
NDA20-789, Zonegran (zonisamide) Capsules 100 mg, FDA Approved Labeling Text, p. 1-24 (Mar. 27, 2000).
Neumeister et al. 1999. Addition of naltrexone to fluoxetine in the treatment of binge eating disorder. Am. J. Psychiatry, 156(5):797.
NIH Publication No. 05-3892, Dec. 2004, National Diabetes Statistics, 18 pp.
Ninan et al., 1992, An improved synthesis of noroxymorphont, Tetrahedron., 48(32):6709-6716.
Niswender et al. 1997. Effects of increased glucokinase gene copy number on glucose homeostatis and hepatic glucose metabolism. The Journal of Biological Chemistry, 272(36):22570-22575.
Note for guidance on stability testing of existing active substances and related finished product, Committee for Proprietary Medicinal Products (CPMP), Apr. 22, 1998, 9 pp.
Novi et al. (Apr.-Jun. 1990) The role of opioid antagonists in the treatment of obesity. Results of a clinical trial with naltrexone, Minerva Endocrinol. 15(2):121-123, Abstract.
O'Byrne et al., Jan. 1, 1990, Effects of drugs on glucose tolerance in non-insulin-dependent diabetes (part II), Drugs, Adis International Ltd., 40(2):204-219.
Okada et al. (1992) Effects of zonisamide on extracellular levels of monoamine and its metabolite, and on Ca2+ dependent dopamine release Epilepsy Research, 13:113-119.
Okada et al. (1995) Effects of zonisamide on dopaminergic system, Epilepsy Research, 22:198-205.
Olsen et al., (1990) Conjugate Addition Ligands of Opioid Antagonists. Methacrylate Esters and Ethers of 6Alpha- And 6Beta-Naltrexol, Journal of Medicinal Chemistry, American Chemical Society, 33(2):737-741.
Olszewski et al. (Jun. 13, 2001) Evidence of Interactions Between Melanocortin and Opioid Systems in Regulation of Feeding, NeuroReport, 12(8):1727-1730.
Oncken et al., 2001, Adverse effects of Oral naltrexone: an analysis of data from two clinical trials, Psychopharmacology, 154:397-402.
Oommen et al. (1999) Zonisamide: A new antiepileptic drug. Clinical Neuropharmacology, 22(4):192-200.
Orexigen Therapeutics Press Release: "Orexigen Therapeutics Provides Statement on Termination of the Light Study and Updates on Contrave Collaboration with Takeda Pharmaceuticals", May 12, 2015, retrieved from http://ir.orexigen.com/phoenix.zhtml?c=207034&p=irol-newsArticle_Print&ID=2047312.
Orexigen Therapeutics Press Release: "Takeda Pharmaceuticals and Orexigen Therapeutics Announce Termination of the Cardiovascular Outcomes Study (Light Study) of the Obesity Drug Contrave® (naltrexone HCI and bupropion HCI)", May 12, 2015, retrieved from http://ir.orexigen.com/phoenix.zhtml?c=207034&p=irol-newsArticle_Print&ID=2046959.
Orexigen Therapeutics, Inc., 2008, A safety and efficacy study comparing naltrexone SR/bupropion SR and placebo in obese type 2 diabetics, http://clinicaltrials.gov/ct2/show/NCT00474630, 3 pp.
Orexigen Therapeutics, Inc., Method-of-use study assessing the effect of naltrexone sustained release (SR)/bupropion SR on body weight and cardiovascular risk factors in overweight and obese subjects, http://clinicaltrials.gov/ct2/show/NCT01764386, 5 pp. Feb. 9, 2013.
Ortho-Novum Tablets and Modicon Tablets Prescribing Information, Apr. 2002, 8 pp.
Otake et al. (May 15, 2005) Association of visceral fat accumulation and plasma adiponectin and colorectal ademona: evidence for participation of insulin resistance, Clinical Cancer Research 11:3642-3646.
Ovadia, Oct. 1999, A Novel Twist on Binge Eating Treatment, Psychiatric Dispatches in Primary Psychiatry; 6(10):24-29.
Paar et al., 2002, Bivalent ligands with rigid double-stranded DNA spacers reveal structural constraints on signaling by FcɛRI, J. Immunol., 169:856-864.
Padwal, Oct. 6, 2009, Contrave, a bupropion and naltrexone combination therapy for the potential treatment of obesity, Curr. Opin. Investig. Drugs, 10(10):1117-1125 (abstract).
Pagoto et al., Association of Major Depression and Binge Eating Disorder with Weight Loss in a Clinical Setting, Obesity, Nov. 2007; 15(11):2557-2559.
Paile-Hyvarinen et al., Mar. 14, 2003, Quality of life and metabolic status in mildly depressed women with type 2 diabetes treated with paroxetine: a single blind randomised placebo controlled trial, BMC Family Practice, Biomed Central, 4(1), 6 pp.
Pandit, 2007, Introduction to the Pharmaceutical Sciences, 1st Ed., Lippincott Williams & Wilkins, Baltimore, MD, p. 154.
Pasternak et al. (1980) Long-acting opiate agonists and antagonists: 14-hydroxydihydromorphinone hydrazones, Med. Chem, 23:674-676.
Patel et al., Jun. 2011, A hospital-based observational study of type 2 diabetic subjects from Gujarat, India, Journal of Health, Population and Nutrition, 29(3):265-272.
Pavuluri et al. (2002) Topiramate Plus Risperidone for Controlling Weight Gain and Symptoms in Preschool Mania, Journal of Child and Adolescent Psychopharmacology, 12(3):271-273.
Pearlstein et al., 2003, A double-blind, placebo-controlled trial of fluvoxamine in binge eating disorder; a high placebo response, Arch Womens Ment Health, 6:147-151.
Penn et al., 2003, Pharmacotherapy of obesity in the near term, Current Opinion in Endocrinology and Diabetes, 18(2):311-316.
Pfizer Inc., Apr. 2014, Embeda Prescription Information, 34 pp.
Plodkowski et al., 2009, Bupropion and naltrexone: a review of their use individually and in combination for the treatment of obesity, Expert Opin. Pharmacother. 10(6):1069-1081.
Portoghese et al., 1982, Opioid agonist and antagonist bivalent ligands as receptor probes, Life Sciences, 31:1283-1286.
Portoghese et al., 1986, Opioid agonist and antagonist bivalent ligands. The relationship between spacer length and selectivity at multiple opioid receptors, J. Med. Chem., 29:1855-1861.
Portoghese et al., 1986, Synthesis and Opioid antagonist potencies of naltrexamine bivalent ligands with conformationally restricted spacers J. Med. Chem., 29:1650-1653.
Portoghese, 1992, The role of concepts in structure-activity relationship studies of opioid ligands, J. Med. Chem., 35:1927-1937.
Potter et al., 1997, Sustained Weight Loss Associated with 12-month topiramate Therapy, Epilepsia, Raven Press Ltd. New York, 38(Suppl 8):97.
Ramlo-Halsted et al., 2000, The natural history of type 2 diabetes: practical points to consider in developing prevention and treatment strategies, Clin. Diabetes, 18(2).
Rao et al. (1998) Fixed-dose combination therapy: panacea or poison?, Intensive Care Med, 24:283-285.
Rao, Mar. 2001, Insulin resistance syndrome, American Family Physician, 63(6):1159-1163.
Reaven, G. M. 1995. Pathophysiology of insulin resistance in human disease. Physiological Reviews, 75(3):473-486.
Reents et al. (1988) Nalozone and naltrexone, Chest, 93(1):217-219.
Remington's Pharmaceutical Sciences, 1980, 16th ed., Mack Publishing Company, Arthur Osol. Editor, pp. 1553-1584.
Remington's Pharmaceutical Sciences, 1980, 16th ed., Mack Publishing Company, Arthur Osol. Editor, pp. 1594-1613.
Remington's Pharmaceutical Sciences. 18th Edition; Easton, PA: Mack Publishing Co. (1990).
Reneric et al. (Nov. 1998) Opioid Receptor Antagonists in Psychiatry, CNS Drugs, 10(5):365-382.
Rezvani et al. 2000. Combination pharmacotherapy: A mixture of small doses of naltrexone, fluoxetine, and thyrotropin-releasing hormone analogue reduces alcohol intake in three strains of alcohol-preferring rats. Alcohol & Alcoholism, 35(1):76-83.
Ricca et al., 2001, Fluoxetine and fluvoxamine combined with individual cognitive-behavior therapy in binge-eating disorder: a one-year follow-up study, Psychotherapy and Psychosomatics, 70:298-306.
Richelsen et al., Feb. 1994, Growth hormone treatment of obese women for 5 wk: effect on body composition and adipose tissue LPL activity, Am J. Physiol., 266(2 Pt 1):11-16.

(56) References Cited

OTHER PUBLICATIONS

Romano et al. 2001. Long-term treatment of obsessive-compulsive disorder after an acute response: A comparison of fluoxetine versus placebo. Journal of Clinical Psychopharmacology, 21(1):46-52.

Rotzinger et al. (1999) Metabolism of some 'second' and 'fourth' generation antidepressants: iprindole, viloxazine, bupropion, mianserin, maprotiline, trazadone, nefazodone, and vaniafaxine, Cellular and Molecular Neurobiology, 19:430.

Rowland et al. (2001) Effects of the cannabinoid receptor antagonist SR 141716, alone and in combination with dexfenfluramine or naloxone, on food intake in rats. Psychopharmacology; 159:111-116.

Saba et al. 2002. Lamotrigine-clozapine combination in refractory schizophrenia: Three cases. The Journal of Neuropsychiatry and Clinical Neurosciences, 14(1):86.

Sackellares et al. (1985) Pilot study of zonisamide (1,2-benzisoxazole-3-methanesulfonamide) in patients with refractory partial seizures. Epilepsia, 26(3):206-211.

Saper et al. (2002) The need to feed: Homeostatic and hedonic control of eating, Neuron, 36:199-211.

Sashiwa et al., 2000, Chemical modification of chitosan. 3. Hyperbranched chitosan-sialic acid dendrimer hybrid with tetraethylene glycol spacer, Macromolecules, 33:6913-6915.

Sayre et al., 1984, Design and synthesis of naltrexone-derived affinity labels with nonequilibrium opioid agonist and antagonist activities. Evidence for the existence of different receptor subtypes in different tissues, J. Med. Chem., 27:1325-1335.

Scheen et al., May 1, 2005, Diabete sucre iatrogene: l'exemple des anti-phsychogiques atypiques, Revue Medicale de Liege, 60(5-6):455-460.

Schimmel et al., 1974, Inhibition by diphenylhydantoin of the diabetogenic action ofstreptozocin, Horm. Metab. Res. 6:475-477.

Schmidhammer et al. (1994) Mixed Azines of Naloxone with Dihydromorphinone Derivatives. A. Helv. Chim. Acta; 77:999-1002.

Schmidt et al. (1993) Zonisamide for add-on treatment of refractory partial epilepsy: a European double-blind trial. Epilepsy Research; 15:67-73.

Schneider et al., Sep. 15, 2009, Design and methods for a randomized clinical trial treating comorbid obesity and major depressive disorder, BMC Psychiatry, 8:77.

Shapira et al. (2000) Treatment of Binge-Eating Disorder with Topiramate: A Clinical Case Series. J. Clin. Psychiatry; 61(5):368-371.

Shapira et al. 2004. A double-blind, placebo-controlled trial of olanzapine addition in fluoxetine-refractory obsessive-compulsive disorder. Biol. Psychiatry, 550:553-555.

Shapiro et al. (2005) Additive Benefits of Combination Therapy with Sibutramine and Rimonabant on Body Weight, Insulin Sensitivity and Lipoproteins in Diet-Induced Obese Mice, 2005 NAASO Annual Meeting, Poster 405-P.

Shelton (2003) Classification of Antidepressants and their Clinical Implications, Primary Care Companion J. Clin. Psychiatry, 5(Supp. 7):27-32.

Shriqui et al. (Jul. 2002) Atypical Antipsychotics, The Canadian Journal of CME, pp. 65-80.

Shuman et al., Jun. 1986, Abnormal body fat distribution detected by computed tomography in diabetic men, Investigative Radiology, 21(6):483-487.

Sitsen et al., 2001, Drug-drug interaction studies with mirtazapine and carbamazepine in healthy male subjects, European Journal of Drug Metabolism and Pharmacokinetics, 26(1-2):109-121.

Sleep Disorders, in Diagnostic and Statistical Manual of Mental Disorders, 4th Edition, American Psychiatric Association, p. 583-595 (2000).

Sneer et al., Protective effect of diphenylhydantoin on the diabetes-inducing effect of alioxan, database accession No. 1980:34024.

Spiegel et al., 1987, Effect of naltrexone on food intake, hunger, and satiety in obese men, Physiology & Behavior, 40(2):135-141.

Spigset et al. (2001) Therapeutic Approaches to Bulimia Nervosa, Expert Opinion on Therapeutic Patents, 11(3):463-477.

Srivastava et al. 1975. Organic disulfides and related substances. 38. Some disulfide and trisulfide sulfinate salts as antiradiation drugs. Journal of Medicinal Chemistry, 18(8):798-802.

Stansfeld et al., Aug. 1992, Social class and minor psychiatric disorder in British civil servants: a validated screening survey using the General Health Questionnaire, Psychological Medicine, 22:739-749.

Stedman's Medical Dictionary, 28th ed., Lippincott Williams & Wilkins, Philadelphia, 1999, pp. 490-491 and 1552.

Steffen et al. 2006. Emerging drugs for eating disorder treatment. Expert Opin. Emerging Drugs, 11(2):315-336.

Stein (Feb. 15, 2000) Neurobiology of the obsessive-compulsive spectrum disorders, Biological Psychiatry 47(4):296-304.

Stein (Aug. 3, 2002) Obsessive-compulsive disorder, Lancet 360(9330):397-405.

Stepinski et al., 1991, Use of hydrophilic diamines for bridging of two opioid peptide pharmacophores, Internat. J. of Peptide & Protein Res., 38:588-592.

Storch et al. 2006. Clinical predictors of early fluoxetine treatment response in obsessive-compulsive disorder. Depression and Anxiety, 23:429-433.

Stromberg et al. (2002) A comparison of the effects of 6-beta naltrexol and naltrexone on the consumption of ethanol or sucrose using a limited-access procedure in rats. Pharmacology, Biochemistry, and Behavior, 72:483-490.

Swedo et al. 1998. Pediatric autoimmune neuropsychiatric disorders associated with *Streptococcal* infections: Clinical description of the first 50 cases. Am. J. Psychiatry, 155(2):264-271.

Symons et al. 2004. Self-injurious behavior and the efficacy of naltrexone treatment: A quantitative synthesis. Mental Retardation and Developmental Disabilities Research Reviews, 10:193-200.

Tallarida et al., 1996, Testing for synergism over a range of fixed ratio drug combinations: replacing the isobologram, Life Sciences, 58(2):PL23-PL28.

Tallarida, 2001, Drug synergism: its detection and applications, J. Pharmacol. and Expt. Therap., 298(3):865-872.

Tamiz et al., 2000, Application of the bivalent ligand approach to the design of novel dimeric serotonin reuptake inhibitors, J. Am. Chem. Soc., 122:5393-5394.

Tamiz et al., 2001, Pharmacological and behavioral analysis of the effects of some bivalent ligand-based monoamine reuptake inhibitors, J. Med. Chem., 44:1615-1622.

Tavakoli et al., Jul. 2003, Diabetic ketoacidosis in a patient with olanzapine, valproic acid, and venlafaxine, Southern Medical Journal, 96(7):729-730.

Testa, 2004, Prodrug research: futile or fertile?, Biochemical Pharmacology, 68:2097-2106.

Thearle et al. (2003) Obesity and Pharmacology, Endocrinology and Metabolism Clinics of North American, W.B. Suanders Company, Philadelphia US 32(4):1005-1024.

Thombre et al. (2004) Osmotic drug delivery using swellable-core technology, Journal of Controlled Release 94:75-89.

Tollefson et al. (1997) Olanzapine versus haloperidol in the treatment of schizophrenia and schizoaffective and schizophreniform disorders: results of an international collaborative trial, Am J. Psychiatry, 154(5):457-465.

Trexan® (naltrexone hydrochloride), in Physicians' Desk Reference, 49th edition, 1995, pp. 965-967.

Turnbull et al., Jan. 1985, The effect of valproate on blood metabolite concentrations in spontaneously diabetic, ketoacidotic, bb/e wistar rats, Diabetes Research 2(1):45-48.

Tutka et al., 2004, Convulsant and anticonvulsant effects of bupropion in mice, European Journal of Pharmacology, 499:117-120.

Van Schaftingen et al. (1992) The regulatory protein of liver glucokinase. Advan. Enzyme Regul., 32:133-148.

Verebey, 1981, Quantitative determination of naltrexone, 6 β-naltrexol and 2-hydroxy-3-methoxy-6 β-naltrexol (HMN) in human plasma, red blood cells, saliva and urine by gas liquid chromatography, National Institute on Drug Abuse Research Monograph Series 28:36-51.

(56) References Cited

OTHER PUBLICATIONS

Verebey, 1981, The clinical pharmacology of naltrexone: pharmacology and pharmacodynamics, National Institute on Drug Abuse Research Monograph Series 28:147-158.
Vieta et al. (2003) 1-year follow-up of patients treated with risperidone and topiramate for a manic episode, J Clin Psychiatry, 64(7):834-829.
Vieta et al. (2004) Effects on weight and outcome of long-term olanzapine-topiramate combination treatment in bipolar disorder. Journal of Clinical Psychopharmacology 24(4):374-378.
Vythilingum et al. 2005. Obsessive-compulsive disorders and dermatologic disease. Dermatologic Clinics, 23:675-680.
Wadden et al. (2000) Effects of Sibutramine Plus Orlistat in Obese Women Following 1 Year of Treatment by Sibutramine Alone: A Placebo-Controlled Trial, Obesity Research; 8(6):431.
Wadden et al., Jan. 2011, Weight loss with naltrexone SR/bupropion SR combination therapy as an adjunct to behavior modification: the COR-BMOD trial, Obesity, 19(1):110-120.
Walker et al. (1988) Chronic Toxicity of the Anticonvulsant Zonisamide in Beagle Dogs, Fundamental and Applied Toxicology 11:333-342.
Wall et al., Jul./Aug. 1981, Metabolism and disposition of naltrexone in man after oral and intravenous administration, Drug Metabolism and Disposition, 9(4):369-375.
Wang et al. (2002) Gabapentin augmentation therapy in bipolar depression, Bipolar Disorders 4:296-301.
Weintraub et al. (1992) Long-term Weight Control Study I (weeks 0 to 34) 'The Enhancement of Behavior Modification, Caloric Restriction, and Exercise by Fenfluramine Plus Phentermine versus Placebo', Clinical Pharmacology & Therapeutics, 51(5):586-94.
Wellbutrin® (bupropion hydrochloride) tablets, in Physicians' Desk Reference, 49th edition, 1995, pp. 824-827, 150.
Welty et al. (Nov. 30-Dec. 5, 2001) Weight Loss Associated With Use of Zonisamide in European and US Clinical Trials, A Compendium of Posters and Platform Sessions for Zonegran®, Presented at the Annual Meeting 2001 of the American Epilepsy Society, Philadelphia, Pennsylvania.
Wermuth, Apr. 2006, Similarity in drugs: reflections on analogue design, Drug Discovery Today, 11(7/8):348-354.
Werneke et al. (2002) Options for Pharmacological Management of Obesity in patients Treated with Atypical Antipsychotics, International Clinical Psychopharmacology, 17(4):145-160.
Wheatley et al., 1998, Mirtazapine: efficacy and tolerability in comparison with fluoxetine in patients with moderate to severe major depressive disorder, J. Clin Psychiatry, 59(6):306-312, Abstract.
White et al. 2002. Development and validation of the food-craving inventory. Obesity Research, 10(2):107-114.
White et al., 2003, Clarifying the role of insulin in type 2 diabetes management, Clinical Diabetes, 21(1):14-21.
Wieczorek et al., 2001, The effects of the selective serotonin reuptake-inhibitor fluvoxamine on body weight in Zucker rats are mediated by cortocotrophin-releasing hormone, International Journal of Obesity, 25(10):1566-1569.
Wilcox et al., 2009, An open-label study of naltrexone and bupropion combination therapy for smoking cessation in overweight and obese subjects, Addictive Behaviors, 35(3):229-234.
Wilding (2004) Clinical evaluation of anti-obesity drugs. Current Drug Targets; 5:325-332.
Willmore, L. J. 2004. Commentary on Leppik. Seizure, 13S:S10.
Wilner, 2002, Is Weight Loss With Zonisamide Gender-Specific?, Annual Meeting of the American Epilepsy Society, https://secure.neurohub.net/cgi-perl/get.cgi?pub=52318&ext=htm, 1 pp.
Winstanley et al., 1989, The effects of food on drug bioavailability, Br. J. clin. Pharmac. 28:621-628.
Wolff (1995) Burger's Medicinal Chemistry and Drug Discovery, John Wiley & Sons, 5th Ed. 1:975-977.
Wong et al., Aug. 2004, Starting insulin treatment in type 2 diabetes, Australian Prescriber, 27(4):93-96.
Yeomans et al. (2002) Opioid peptides and the control of human ingestive behaviour, Neuroscience and Biobehavioral Reviews, 26:712-728.

Yoshimasu et al. (2003) Psychotropic Drug-Induced Obesity, Nippon Rinsho, 61(Suppl. 6):825-829. (English translation of Japanese Office Action containing Examiner's characterization of reference is appended to reference: Notice of Reasons for Rejection, Application No. 2006-549530).
Yu et al. (2005) Influence of insulin treatment on insulin sensitivity in insulin requiring type 2 diabetes patents, Diabetes Research and Clinical Practice, 6881:854-859.
Zeng et al., 1988, Convenient synthesis of 9-alkyl and 9-arylacridines from [2-(trimethylsilyl)ethoxy]methyl (sem) protected acridone, Tetrahedron Letters, 29(40):5123-5124.
Zhang et al. (1994) Positional Cloning of the Mouse obese gen and its humane homologue, Nature, 372:425-432.
Zhu et al. (Apr. 3, 2002) Pharmacologic Treatment of Eating Disorders, Canadian Journal of Psychiatry, 47(3):227-234.
Zitterl et al. 1999. Efficacy of fluoxetine in Austrian patients with obsessive-compulsive disorder. Wiener Klinische Wochenschrift, 111(11):439-442.
Zohar et al. 1987. Serotonergic responsivity in obsessive-compulsive disorder. Arch. Gen. Psychiatry, 44:946-951.
Zonisamide (Oral Route), MayoClinic.com, 12 pp., 2009.
ISR and WO for PCT/US07/084177, dated May 20, 2008.
IPRP for PCT/US07/084177, dated May 22, 2009.
Anonymous, Jun. 7, 2008, Orexlgen® Therapeutics announces that Contrave® may reverse the incidence of metabolic syndrome, PipelinReview.com.
Anonymous, Nov. 24, 2013, Positive interim analysis of the light study, testing weight loss medication, Physicans' Academy for Cardiovascular Education—News, Orexlgen press release.
Chilton et al., Oct. 2, 2011, Neltraxone SR/Bupropion SR combination therapy improves predicted 10-year risk of cardiovascular disease, coronary heart disease, myocardial infarcation, and congestive heart failure, Obesity, 19(Suppl 1):S177.
Cleary et al., Jul. 1996, Naloxone effect on sucrose-motivated behavior, Psychopharmacology (Berl.), 126(2):110-114.
ClinicalTrials.gov archive, Feb. 5, 2010, A phase 3 study comparing the safety and efficacy of two doses of naltrexone sustained release (SR)/bupropion sustained release (SR) and placebo in obese subjects, NCT00532779, 3 pp.
ClinicalTrials.gov, Dec. 20, 2006, Placebo-controlled trial of bupropion for the treatment of binge eating disorder, https://clinicaltrials.gov/ct2/show/study/NCT00414167, 3 pp.
Contrave (naltrexone HCI and bupropion HCI) extended-release tablets, initial U.S. approval, 2014.
Defendant Actavis Laboratories FL, Inc.'s Initial Invalidity Contentions for U.S. Patent Nos. 7,375,111, 7,462,626, and 8,916,195, in *Takeda Pharmaceutical Company Limited et al.*, Plaintiffs, v. *Actavis Laboratories FL, Inc.*, Defendant, C.A. No. 15-451-RGA, US District Court for the District of Delaware, dated Dec. 23, 2015, 147 pp.
Dramatic alcohol treatment results seen with naltrexone, Psychiatric Times, Sep. 1, 1998, 5 pp.
Fava, 2005, 15 years of clinical experience with bupropion HCI: from bupropion to bupropion SR to bupropion XL, Prim, Care Companion J. Clin Psychiatry, 7:106-113.
Ghisoli et al., 1980, Effects of dopaminergic receptor stimulation and opioid receptor blockade on GH incretion: preliminary findings, Boll. Soc. Ital. Biol. Sper., 56(12):1222-1225.
GlaxoSmithKline, Jun. 2009, Prescribing Information: Wellbutrin® (bupropion hydrochloride) Tablets, pp. 4-32.
Greenway et al., Jun. 10, 2008, Naltrexone and bupropion reduce the prevalence of the metabolic syndrom, Diabetes, 57(Suppl. 1), Abstract No. 2735-PO.
Miller et al., May 2006, Metabolic syndrome: screening, diagnosis, and management, Journal of Midwifery & Women's Health, 51(3):141-151.
Minnaro et al., 1997, Aspectos technologicos de las formas farmaceuticas de liberacion modificada de administracion oral: sistemas matriciales, flotantes y bioadhesivos, Cienc. Pharm, 7(3):113-121.
NIH News Release, First federal obesity clinical guidelines released, Jun. 17, 1998, 3 pp.
O'Neil et al., Oct. 3, 2011, Naltrexone SR/Bupropion SR and intensive behavioral modification combination increases the likeli-

(56) References Cited

OTHER PUBLICATIONS hood of achieving early and sustained weight loss and associated improvement in markers of cardiometabolic risk, Obesity, 19(Suppl 1):S179-S180.
Orexigen Therapeutics Press Release, Feb. 1, 2011, FDA issues complete response to new drug application for Contrave® for the management of obesity, 3 pp.
Padwal et al., Oct. 2009, Contrave, a bupropion and naltrexone combination therapy for the potential treatment of obesity, Current Opinion in Investigational Drugs, 10:1117-1125.
Remington: The Science and Practice of Pharmacy, 20th Ed., Chapter 45: Oral Solid Dosage Forms, pp. 858-893, 2003.
Remington's Pharmaceutical Sciences, 1980, 16th ed., Mack Publishing Company, Arthur Osol. Editor, pp. 1592-1597, 1676-1678.
Shikh, Jan. 27, 2007, Bioavailablity of oral medications, Russian Medical Journal, 2:95.
Sneer et al., 1979, Revista medico-chirurgicala, 83(1):87-91.
Thorndike, Jan. 28, 2008, Depressive symptoms and smoking cessation after hospitalization for cardiovascular disease, Arch Intern Med, 168(2):186-191.
Van Gaal et al., Aug. 1998, Sibutramine and fat distribution: is there a role for pharmacotherapy in abdominal/visceral fat reduction?, Int J Obes Relat Metab Disord, Suppl 1:S38-40; discussion S41-2.
White et al., 2013, Buproprion for overweight women with binge-eating disorder: a randomized, double-blind, placebo-controlled trial, J. Clin. Psychiatry, 74(4):400-406.
www.1000mealplans.com (accessed Feb. 21, 2017), 2 pp.
Greenway et al. "Weight Loss with Bupropion and Naltrexone Improves Markers of Insulin-Resistance." ADA 67th Scientific Sessions, Category 20B, Poster 45LB, Jun. 23, 2007. Retrieved from: https://assets.cureus.com/uploads/poster/file/277/converted_ADA_2007_Abstract.png.

\* cited by examiner

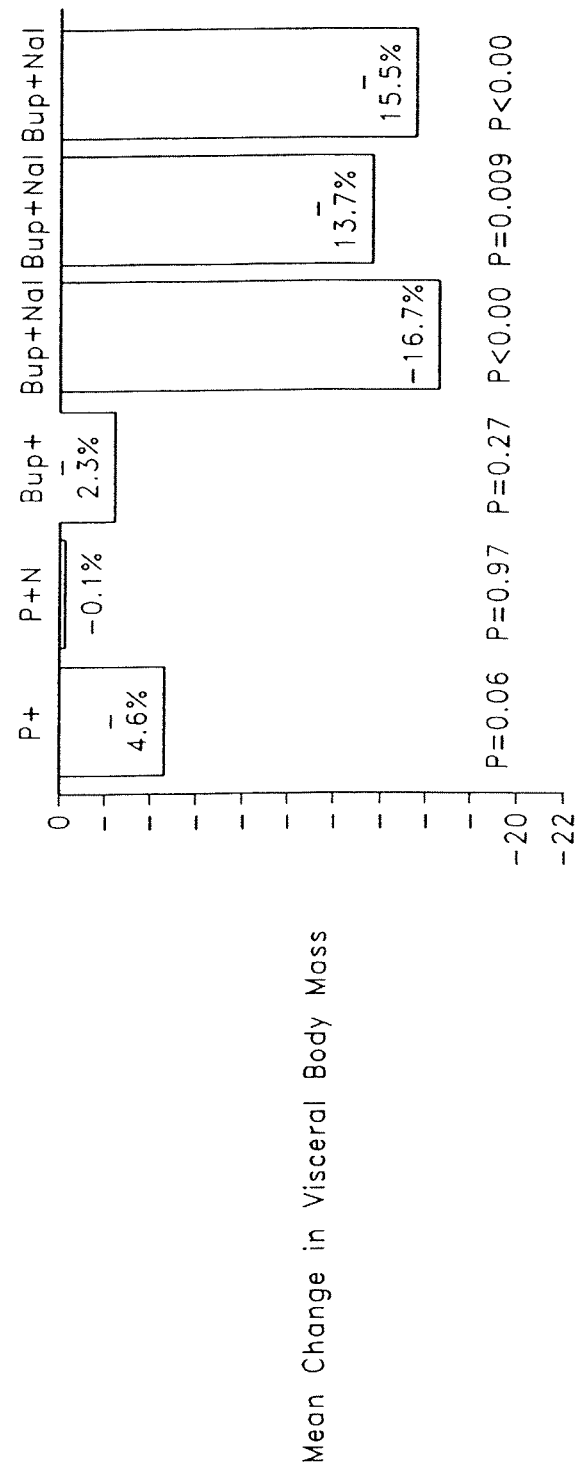

METHODS FOR TREATING VISCERAL FAT CONDITIONS

RELATED APPLICATION INFORMATION

The present application is a continuation of U.S. application Ser. No. 14/584,985, filed Dec. 29, 2014, which is a continuation of U.S. application Ser. No. 12/995,121, filed Feb. 28, 2011, which is the U.S. National Phase under 35 U.S.C. § 371 of International Application No. PCT/US2009/045720, entitled "METHODS FOR TREATING VISCERAL FAT CONDITIONS," filed May 29, 2009, and published in English on Dec. 30, 2009 as WO 2009/158114 A1, which claims the benefit of priority to U.S. Provisional Application No. 61/057,743, filed May 30, 2008, all of which are hereby incorporated by reference in their entireties. Any and all applications for which a foreign or domestic priority claim is identified in the Application Data Sheet as filed with the present application, or any correction thereto, are hereby incorporated by reference under 37 CFR 1.57.

BACKGROUND OF THE INVENTION

Field of the Invention

Embodiments of the present invention relate to methods and compositions for reducing visceral fat and/or treating metabolic syndrome.

Description of the Related Art

Health risks associated with obesity can depend on how and where the fat is stored. Cutaneous fat refers to fat that is near the skin's surface. Visceral fat, which may also be referred to as intra-abdominal or subcutaneous fat, typically surrounds internal organs. In contrast to subcutaneous fat, visceral fat has been shown to be a risk factor associated with a variety of serious medical disorders.

For example, whether a person is obese (BMI>30) or not, they can still experience visceral fat accumulation in the abdominal cavity (particularly, in the mesentery and/or in the greater omentum). This accumulation, in turn, is often positively correlated with elevated values of serum cholesterol, triglyceride, and/or blood glucose measured by the glucose tolerance test. Visceral fat accumulation also often positively correlates with the systolic and diastolic blood pressures, and accordingly is related to a heightened risk of diseases such as hypertension, diabetes, and hyperlipemia (see, e.g., Fujioka, S., et al. Metabolism, 36 54-59, 1987; Matsuzawa, Y., et al. Progress in Obesity Research, 309-312, 1990). These diseases are therefore thought to be treated, cured and/or prevented by decreasing visceral fat, by inhibiting visceral fat accumulation, and/or improving body fat distribution (see, e.g., Bray, G. A., Obesity Research, 3, Suppl. 4, 425S-434S, 1995). Hence, there is a need for an effective pharmacotherapy for decreasing visceral fat.

SUMMARY OF THE INVENTION

In some embodiments, a method of treating a visceral fat condition is provided. The method can include identifying a person in need thereof; and administering to the person naltrexone and bupropion in dosages that together are effective to treat the visceral fat condition. Identifying the person in need of treatment can include determining that the person is viscerally obese and/or determining that the person has an amount of visceral fat that increases the risk and/or severity of at least one disease or condition selected from coronary heart disease, cancer, diabetes, glucose intolerance, hyperinsulinemia, hypertension, periodontal disease and a metabolic syndrome. Identifying the person in need of treatment can include determining a patient waist-to-hip measurement ratio. The patient's waist-to-hip measurement ratio can be about 0.8 or greater. Identifying the person in need of treatment can include analyzing one or more test selected from a computed tomography (CT) scan, a magnetic resonance imaging scan, and an ultrasonogram. The intra-abdominal fat area of the person, as determined by CT scanning in a single tomographic slice at the $L_4$-$L_5$ level can be about 80 $cm^2$ or greater. Identifying the person in need of treatment can include determining that the body mass index of the person is greater than about 25, greater than about 27, greater than about 30, or greater than about 40. Naltrexone and bupropion can be administered together in a single dosage form. The bupropion dosage for an adult human can advantageously be in the range of from about 100 mg to about 600 mg, for example, about 100 mg, about 150 mg, about 200 mg, about 250 mg, about 300 mg, about 350 mg, about 400 mg, about 450 mg, about 500 mg, about 550 mg, or about 600 mg. The naltrexone dosage for an adult human can be in the range of from about 4 mg to about 50 mg, for example, about 4 mg, about 8 mg, about 16 mg, about 32, mg or about 48 mg. Identifying the person in need of treatment can include determining that the person has metabolic syndrome (also known as Syndrome X), which can include identifying at least three patient characteristics selected from abdominal obesity, elevated triglyceride levels, decreased high-density lipoprotein (HDL) cholesterol levels, high blood pressure, and impaired fasting blood glucose. The naltrexone and bupropion can be administered in dosages that together are effective to result in at least one effect selected from a reduction of abdominal obesity, a reduction of triglyceride levels, an increase of high-density cholesterol levels, a reduction in blood pressure, and an improvement in fasting blood glucose levels. In some cases, the body mass index of the person can be greater than about 25 (definition of overweight), greater than about 27, greater than about 30 (definition of obesity) or greater than about 40, whereas in other cases the body mass index of the patient can be less than about 30 (non-obese). In any case, visceral fat and its health consequences can be present. The naltrexone and bupropion can be administered in dosages that together are effective to additionally result in a reduction of inflammation, which can include reduction of the serum level of interleukin 6 and/or a reduction of the serum level of C-reactive protein. Such factors are believed to mediate cardiovascular risk. Thus, the naltrexone and bupropion can be administered in dosages that together are effective in reducing the person's susceptibility to a heart disease.

A method of treating a visceral fat condition can also include administering naltrexone or a pharmaceutically acceptable salt thereof and bupropion or a pharmaceutically acceptable salt thereof to a person who has been identified or diagnosed as being in need of treatment for a visceral fat condition in order to treat the visceral fat condition. Naltrexone or a pharmaceutically acceptable salt thereof can be administered in an amount effective to enhance the treatment effect of bupropion or a pharmaceutically acceptable salt thereof compared to the administration of bupropion or a pharmaceutically acceptable salt thereof alone. Bupropion or a pharmaceutically acceptable salt thereof can be administered in an amount effective to enhance the treatment effect of naltrexone or a pharmaceutically acceptable salt thereof compared to the administration of naltrexone or a pharmaceutically acceptable salt thereof alone. The person can have an amount of visceral fat that increases the risk and/or severity of at least one disease or condition selected from coronary heart disease, cancer, diabetes, glucose intolerance, hyperinsulinemia, hypertension, periodontal disease, and a metabolic syndrome. The person can previously have been identified or diagnosed using a method comprising the determination of a waist-to-hip measurement ratio. The waist-to-hip measurement ratio can be about 0.8 or greater. The person can previously have been identified or diagnosed using a method comprising analyzing one or more test selected from a computed tomography (CT) scan, a magnetic resonance imaging scan, and an ultrasonogram. The intra-abdominal fat area of the person, as determined by CT scanning in a single tomographic slice at the $L_4$-$L_5$ level, can be about 80 $cm^2$ or greater. The person can have metabolic syndrome. Metabolic syndrome could have been identified or diagnosed using a method comprising identifying at least three patient characteristics selected from abdominal obesity, elevated triglyceride levels, decreased high-density lipoprotein (HDL) cholesterol levels, high blood pressure, and impaired fasting blood glucose. The treatment of a visceral fat condition can reduce the person's susceptibility to a heart disease. This reduction can include a reduction of inflammation, a reduction in the serum level of interleukin 6, and/or a reduction of the serum level of C-reactive protein. The person can be viscerally obese. In some cases, the body mass index of the person can be greater than about 30 (i.e., obese). In some cases, the body mass index of the person can be greater than about than about 40. In other cases, the body mass index of the patient can be less than about 30 (i.e., non-obese). In any case, visceral fat and its health consequences can be present. Naltrexone or a pharmaceutically acceptable salt thereof and bupropion or a pharmaceutically acceptable salt thereof can be administered together in a single dosage form, or can be administered in separate dosage forms. Naltrexone or a pharmaceutically acceptable salt thereof can be administered prior to, concurrently with, or subsequent to bupropion or a pharmaceutically acceptable salt thereof. The bupropion dosage for an adult human can advantageously be in the range of from about 100 mg to about 600 mg, i.e., about 100 mg, about 150 mg, about 200 mg, about 250 mg, about 300 mg, about 350 mg, about 400 mg, about 450 mg, about 500 mg, about 550 mg, or about 600 mg. The naltrexone dosage for an adult human can be in the range of from about 4 mg to about 50 mg, i.e., about 4 mg, about 8 mg, about 16 mg, about 32 mg, or about 48 mg. Naltrexone can be a sustained-release naltrexone and/or bupropion can be a sustained-release bupropion.

In some embodiments, a method of administering visceral fat treatment to a patient is provided. The method includes advising the patient or a care provider that combined therapy with bupropion and naltrexone is effective to treat a visceral fat condition; and administering naltrexone and bupropion to the patient in dosages that together are effective to treat the visceral fat condition. Advising the patient or care provider can include providing written information. The written information can include a label or product insert. Advising the patient or care provider can further include advising that the dosages of naltrexone and bupropion are together effective to result in weight loss.

In some embodiments, a method of treating metabolic syndrome is provided, comprising identifying a person suffering from metabolic syndrome; and administering to the person naltrexone and bupropion in dosages that together are effective to treat metabolic syndrome. Determining that the person has metabolic syndrome can include identifying at least three patient characteristics selected from abdominal obesity, elevated triglyceride levels, decreased high-density lipoprotein (HDL) cholesterol levels, high blood pressure, and impaired fasting blood glucose. One of the characteristics can be abdominal obesity. The naltrexone and bupropion can be administered in dosages that together are effective to result in at least one effect selected from a reduction of abdominal obesity, a reduction of triglyceride levels, an increase of high-density cholesterol levels, a reduction in blood pressure, and an improvement in fasting blood glucose levels. The naltrexone and bupropion can be administered together in a single dosage form. The dosage of the bupropion can be in the range of from about 100 mg to about 600 mg. The dosage of the bupropion can be about 100 mg, about 150 mg, about 200 mg, about 250 mg, about 300 mg, about 350 mg, about 400 mg, about 450 mg, about 500 mg, about 550 mg or about 600 mg. The dosage of the naltrexone can be in the range of from about 4 mg to about 50 mg, for example, about 4 mg, about 8 mg, about 16 mg, about 32 mg or about 48 mg.

These and other embodiments are described in greater detail below.

BRIEF DESCRIPTION OF THE DRAWINGS

FIG. 1 shows average change in visceral body mass following various treatments.

DETAILED DESCRIPTION OF THE PREFERRED EMBODIMENTS

Definitions

The term "visceral fat" as used herein has its ordinary meaning as understood by those skilled in the art and includes the fat in the abdominal region which is inside the peritoneal cavity, and thus is distinct from "subcutaneous fat". Visceral fat can be assessed, either qualitatively or quantitatively, by standard assays known to those of ordinary skill in the art, for example, by computer tomography (CT), magnetic resonance imaging (MRI), ultrasonography, and/or determinations of subject waist-to-hip measurement ratios.

The term "visceral fat condition" as used herein refers to various diseases, conditions and disorders associated with the presence of excessive amounts of visceral fat. An individual having a visceral fat condition thus has an unhealthy amount of visceral fat, e.g., an amount that correlates with increased risk or severity of a disease, condition or disorder associated with the presence of visceral fat. For example, visceral fat is associated with diseases and conditions such as obesity, coronary heart disease, cancer, diabetes, glucose intolerance and hyperinsulinemia (see Montague, C T et al., 2000, Diabetes 49:883-888); hypertension (see Watanabe et al., 2003, Clin Exp Hypertens 25:199-208); periodontal disease (see Wood N et al., 2003, J Clin Periodontol 30:321-327); and metabolic syndromes, such as type II diabetes (see Goodpaster, B H et al., 2003 Diabetes Care 26:372-379). The aforementioned articles are hereby incorporated by reference in their entireties and particularly for the purpose of describing visceral fat conditions. Without being bound by any particular theory, visceral fat is thought (at least) to put a greater fatty acid burden on the liver, causing, complicating, and/or aggravating various diseases and conditions.

The term "selective visceral fat condition" as used herein refers to various diseases, conditions, and disorders associated with the presence of excessive amounts of visceral fat, but not with the presence of excessive amounts of non-visceral (e.g., subcutaneous) fat. For example, a person suffering from visceral obesity but not from obesity in general is suffering from a selective visceral fat condition.

As used herein, "treatment" or "treating" refers to inhibiting or reversing the progression of a disease, condition, or disorder, e.g., visceral obesity, or delaying the onset of a disease, condition, or disorder, e.g., visceral obesity, whether physically, e.g., stabilization of a discernible symptom, physiologically, e.g., stabilization or reduction of a physical parameter, or both. As used herein, the terms "treatment," "treating," and the like, refer to obtaining a desired pharmacologic and/or physiologic effect. The effect can be prophylactic in terms of completely or partially preventing a disease or condition, or a symptom thereof and/or can be therapeutic in terms of a partial or complete reversal, amelioration, or cure for a disease, condition or disorder and/or of an adverse affect attributable to the disease, condition or disorder. "Treatment" or "treating," as used herein, encompasses any treatment of a disease, condition, or disorder in a human, and includes: decreasing the risk of death due to the disease; preventing the disease or disorder from occurring in a subject which may be predisposed to the disease but has not yet been diagnosed as having it; inhibiting the disease or disorder, i.e., arresting its development (e.g., reducing the rate of disease progression); and relieving the disease, i.e., causing regression of the disease. Therapeutic benefits of the treatment methods described herein include reducing the risk of onset or severity of visceral fat conditions as well as improvements in appearance (e.g., the treatment can be a "cosmetically effective" treatment, which can be further associated with improved physical appearance, psychological benefits, emotional benefits, and the like).

As used herein, "enhance," "enhancement," or "enhancing" refers to improving and/or augmenting the therapeutic effect of a compound in the treatment of a disease, condition, or disorder (e.g., a visceral fat condition). A first compound can enhance a second compound by allowing less of the second compound to be administered with an equivalent therapeutic effect. A first compound can enhance a second compound by generating a therapeutic effect that is greater than the therapeutic effect of the second compound administered alone. In some cases, the combination of a first and a second compound has less than an additive therapeutic effect. For example, amounts of naltrexone and bupropion can be selected such that the combination reduces a visceral fat condition to an extent that is less than the sum of naltrexone and bupropion administered alone. In some cases, the combination of a first and a second compound has an additive therapeutic effect. For example, amounts of naltrexone and bupropion can be selected such that the combination reduces a visceral fat condition to an extent that is approximately equal to the sum of naltrexone and bupropion administered alone. In some cases, the combination of a first and a second compound has a synergistic therapeutic effect. For example, amounts of naltrexone and bupropion can be selected such that the combination reduces a visceral fat condition to an extent that is more than the sum of naltrexone and bupropion administered alone.

The term "subcutaneous fat" as used herein has its ordinary meaning as understood by those skilled in the art and includes fat deposited just under the skin, e.g., under the skin of the thigh area.

The term "bupropion" as used herein, unless the context indicates otherwise, includes free bupropion, active bupropion metabolites (including, but not limited to, hydroxybupropion, and the amino-alcohol isomers threohydrobupropion and erythrohydrobupropion), prodrug esters, amides, and pharmaceutically acceptable salts of bupropion, such as (but not limited to) bupropion hydrochloride and bupropion hydrobromide. Bupropion can be formulated as an immediate-release form or a controlled-release form, e.g., a sustained-release form. Bupropion can be formulated for once daily administration.

The term "naltrexone" as used herein, unless the context indicates otherwise, includes free naltrexone, active naltrexone metabolites (including, but not limited to, 6 beta-naltrexol), prodrug esters, amides, and pharmaceutically acceptable salts thereof. Naltrexone can be formulated as an immediate-release form or a controlled-release form, e.g., a sustained-release form as described in U.S. Patent Publication No. 2007-0281021 A1, which is hereby incorporated by reference in its entirety and particularly for the purpose of describing sustained-release forms of naltrexone.

In various embodiments, naltrexone and bupropion are coadministered to a person. Naltrexone and bupropion can be formulated and administered in various ways. See, e.g., U.S. Pat. Nos. 5,512,593 and 5,817,665, as well as U.S. Patent Publication Nos. 2004-0254208 and 2006-0142290, all of which are hereby incorporated by reference in their entireties and particularly for the purpose of describing formulations of naltrexone and bupropion and methods of administering them. Naltrexone and bupropion can be combined into a single dosage form, e.g., in a multilayer tablet as described in U.S. application Ser. No. 11/937,421, filed Nov. 8, 2007, which is hereby incorporated by reference in its entirety and particularly for the purpose of describing multilayer dosage forms comprising naltrexone and bupropion. Alternatively, naltrexone and bupropion can be administered as separate dosage forms, e.g., as described in U.S. application Ser. No. 11/937,367, filed Nov. 8, 2007, which is hereby incorporated by reference in its entirety and particularly for the purpose of describing methods of administering naltrexone and bupropion as separate dosage forms. For example, naltrexone can be administered prior to, concurrently with, or subsequent to bupropion. Coadministration of naltrexone and bupropion, whether simultaneous or temporally separated, should be done so as to provide the two drugs in the blood stream simultaneously, in effective amounts. The dosages discussed herein, when administered simultaneously, provide one example of such effective amounts. One or both of naltrexone and bupropion can be administered with another weight-reducing agent and/or visceral-fat reducing agent. One or both of the naltrexone and bupropion can be in a sustained-release form. For example, in a preferred embodiment, sustained-release naltrexone and sustained-release bupropion are administered concurrently, e.g., as described in U.S. application Ser. Nos. 11/937,421 and 11/937,367.

In some embodiments, one or both of the compounds are formulated for parenteral administration by injection, e.g., by bolus injection or continuous infusion. Formulations for injection can be presented in unit dosage form, e.g., in ampoules or in multi-dose containers, with an added preservative. The compounds can take such forms as suspensions, solutions, or emulsions in oily or aqueous vehicles, and can contain formulatory agents such as suspending, stabilizing, and/or dispersing agents. In some embodiments, a once-monthly injectable form of naltrexone (commercially available under the tradename VIVITROL®) is used for the methods and compositions described herein.

In various embodiments, the present invention relates to a method of treating a visceral fat condition, comprising identifying a person in need thereof and administering to the person naltrexone and bupropion in dosages that together are effective to treat the visceral fat condition. Methods can comprise diagnosing a patient with a visceral fat condition and/or a selective visceral fat condition and administering or providing to the person naltrexone and bupropion in dosages that together are effective to treat the condition. The effectiveness of the treatment can be evidenced by a reduction in visceral fat and/or a reduction in the risk and/or severity of the disease, condition or disorder associated with the presence of the visceral fat. Changes in visceral fat level can be determined by comparing measurements of visceral fat before and after a period of visceral fat treatment as described herein, using a visceral fat measurement technique such as computed tomography (CT), magnetic resonance imaging (MRI), ultrasonography, and/or measuring a change in a treated patient's waist-to-hip measurement ratio. In an embodiment, treatment as described herein results in reductions in visceral fat and subcutaneous fat that are about the same (non-selective), and generally results in overall weight loss. A selective reduction in visceral fat results in a greater reduction in visceral fat than subcutaneous fat, and can even be accompanied by no loss or a gain in subcutaneous fat. Thus, a selective reduction in visceral fat typically involves a redistribution of fat, accompanied by an overall loss of body fat in some situations, whereas in others the redistribution is not accompanied by an overall loss of body fat. Redistribution of body fat is, without being held to theory, one possible explanation for reduction of visceral fat in a subject without an overall reduction in body weight or BMI, which can be due to, for example, a proportional or non-proportional increase in subcutaneous fat.

In general, a decrease in the waist measurement of a treated person that is greater than the decrease in hip measurement indicates that visceral fat is selectively reduced. For example, a selective reduction in visceral fat is indicated where the waist diameter measurement decreases by at least about 1 cm more than the hip measurement, or at least about 2 cm or more than the hip measurement, e.g., about 3 cm to about 5 cm or more than the hip measurement. The waist measurement (or "abdominal perimeter") takes into account both visceral and subcutaneous fat, while the hip measurement takes into account primarily subcutaneous fat. A selective reduction in visceral fat can be evaluated by, for example, determining a reduction of a waist-to-hip measurement ratio from greater than about 1 (where the measurement of the waist circumference and the measurement of the hip circumference are about the same) to a ratio of less than about 1 (wherein the measurement of the waist circumference is less than the measurement of the hip circumference). A selective reduction in visceral fat can also be evaluated by, for example, determining a reduction in the waist-to-hip measurement ratio of greater than about 2%, including about 3% to about 100%, such as by about 4% to about 98%. In some embodiments, a reduction in the waist-to-hip measurement ratio is greater than about 2%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. The percentage reduction in the waist-to-hip measurement ratio can be calculated as one hundred times one minus the patient's initial waist-to-hip ratio divided by the patient's final waist-to-hip ratio ($100*(1-R_i/R_f)$).

Some embodiments of the invention are directed to methods of treating visceral obesity, comprising identifying a person in need of a reduction in visceral fat and administering bupropion and naltrexone to the person in dosages that together are effective to treat the visceral obesity. Visceral obesity is a visceral fat condition in which an overweight or obese person has an excess of visceral fat, e.g., the ratio of visceral fat to subcutaneous fat is higher for the viscerally obese person than for the average non-obese person or person having obesity primarily attributed to subcutaneous fat. Those skilled in the art understand that an obese person is not necessarily viscerally obese, and that a person who has a visceral fat condition is not necessarily obese. Obesity and overweight refer to conditions, as defined by the United States Centers for Disease Control, which are presently defined as an adult subject (a subject of about 20 years of age or older) who presents with a body-mass index (BMI) of about 30 or greater (for obesity) or 25 or greater (for overweight). It will be readily appreciated by those skilled in the art that the BMI-based definition of obesity can be modified to reflect changes in understanding of the condition or practices in the field, and such changes to the BMI-based definitions of obesity and overweight are contemplated herein. For subjects of about 2 to 20 years in age, obesity and overweight are determined using a BMI-for-age calculation, which is plotted on gender specific growth charts (such as those available from the United States Centers for Disease Control). In an embodiment, a viscerally obese person has a BMI of about 30 or greater and a waist-to-hip measurement ratio that is greater than about 1.

Some embodiments of the invention are directed to methods of treating a metabolic syndrome. For example, in an embodiment, naltrexone and bupropion are administered, as described herein, to reduce visceral fat (either the absolute amount of visceral fat or the ratio of visceral fat to subcutaneous fat), and to reduce a symptom, condition, disorder or disease (e.g., a heart disease) associated with a metabolic syndrome. Metabolic syndrome (also known as Syndrome X) represents a group of risk factors that have been linked to obesity and insulin resistance, and are present in about 47 million Americans. This syndrome can increase the risk of later developing diabetes or cardiovascular disease and can be reduced by a loss in excess body weight. Metabolic syndrome (see Adult Treatment panel Guidelines III) is a condition associated with a subject having three or more of the following symptoms: abdominal obesity, elevated triglyceride levels, decreased high-density lipoprotein (HDL) cholesterol levels, high blood pressure, and impaired fasting blood glucose. Abdominal obesity can be manifested for men as greater than a 40-inch waist and for women as greater than a 35-inch waist. Impaired fasting blood glucose can be manifested as 110 mg/dL or higher. Elevated triglyceride levels can be manifested as fasting triglyceride levels of 150 mg/dL or higher. Decreased HDL cholesterol levels can be manifested for men as less than 40 mg/dL and for women as less than 50 mg/dL. High blood pressure can be manifested as 130/85 or higher. Treatment can increase or decrease the measurement of at least one symptom of metabolic syndrome to an amount that no longer falls above or below the threshold to qualify as a symptom. For example, treatment can reduce a waist measurement to less than about 40 inches for a man or less than about 35 inches for a woman, decrease fasting blood glucose to less than about 110 mg/dL, decrease triglyceride level to less than about 150 mg/dL, increase HDL cholesterol level to more than about 40 mg/dL for a man or more than about 50 mg/dL for a woman, and/or reduce blood pressure to less than about 130/85. In some embodiments, treatment reduces the measurement of one or more symptoms such that a subject no longer qualifies as having metabolic syndrome. For example, in some embodiments, the subject has all five symptoms prior to treatment, but only two symptoms during and/or after treatment. In some embodiments, the subject has three symptoms prior to treatment, but has no symptoms during and/or after treatment.

Naltrexone and bupropion can be administered, as described herein as at least part of a prophylactic (prior to onset) and/or cosmetic treatment, wherein the prophylactic and/or cosmetic treatment comprises a relative or absolute reduction of visceral fat. In some instances, the prophylactic and/or cosmetic treatment further comprises weight loss, which may or may not be substantially proportional to the reduction in visceral fat.

Various embodiments are directed to a method of administering a weight loss therapy to a patient, comprising advising the patient or a care provider that combined therapy with bupropion and naltrexone is effective to treat a visceral fat condition. For example, a patient or a care provider can be advised that treatment with naltrexone and bupropion as described herein results in a reduction of visceral body fat and a reduction in the risk and/or severity of at least one disease or condition selected from coronary heart disease, cancer, diabetes, glucose intolerance, hyperinsulinemia, hypertension, periodontal disease and a metabolic syndrome (such as a reduction of abdominal obesity, a reduction of triglyceride levels, an increase of high-density cholesterol levels, a reduction in blood pressure, an improvement in fasting blood glucose levels, a reduction of inflammation, and/or a reduction of the patient's susceptibility to heart disease). The advising can include providing written information. The written information can comprise a label, instructions, or a package insert.

The methods described herein are directed to the treatment of subjects having an excess of visceral fat, which can be manifested as an excessive ratio of visceral fat to subcutaneous fat, by an excessive percentage of total body fat that is attributed to visceral fat, or by an absolute amount of visceral fat that is excessive. For example, the excess of visceral fat can be a level that the subject or a physician considers to be undesirable and/or unhealthy. In certain embodiments, the subjects are obese or overweight, whereas in other embodiment, they are not. The excessively high visceral fat content can include a fat content that increases the risk of medical diseases, conditions, or disorders. The excessively high visceral fat content can include a fat content that is determined to be too high for cosmetic purposes. Identification of the patient can comprise determining or measuring a visceral fat characteristic of a patient. The visceral fat characteristic can include a waist circumference and/or a waist-to-hip ratio. The visceral fat characteristic can be determined at least partially by analyzing one or more of a computed tomography scan, a magnetic resonance imaging scan, and an ultrasonogram.

Naltrexone and bupropion can be administered as described herein to a patient with a waist circumference that is about 80 cm or greater, about 85 cm or greater, about 90 cm or greater, about 95 cm or greater, or about 100 cm or greater. In a preferred embodiment, treatment reduces a patient's waist circumference to less than about 80 cm, or more preferably to less than about 70 cm. Naltrexone and bupropion can be administered as described herein to a patient with a waist-to-hip ratio circumference that is about 0.8 or greater, about 0.85 or greater, about 0.9 or greater, about 0.95 or greater, or about 1 or greater. Naltrexone and bupropion can be administered as described herein to a patient with a waist-to-hip ratio circumference that is about 0.8 or greater, about 0.85 or greater, about 0.9 or greater, about 0.95 or greater, or about 1 or greater. In a preferred embodiment, treatment reduces a patient's the waist-to-hip ratio circumference to less than about 0.8, or more preferably to less than about 0.7. Naltrexone and bupropion can be administered as described herein to a patient with an intra-abdominal fat area, as estimated by CT scanning in a single tomographic slice at the $L_4$-$L_5$ level of about 80 cm$^2$ or greater, about 100 cm$^2$ or greater, about 120 cm$^2$ or greater, or about 130 cm$^2$ or greater. In a preferred embodiment, treatment reduces a patient's tomographic slice at the $L_4$-$L_5$ level to less than about 80 cm$^2$, or more preferably to less than about 70 cm$^2$.

In certain embodiments, the subjects are obese or overweight, whereas in other embodiments, they are not. For example, patients can have a BMI greater than about 25, greater than about 27, greater than about 30, greater than about 40, less than about 30, less than about 40 and/or less than about 50.

Visceral fat levels of subjects can be determined by various techniques known to those skilled in the art. Visceral fat of subjects can be directly measured. Visceral obesity can be diagnosed by determining a subject's waist-to-hip measurement ratio. Generally, measurements are taken of the waist and hip and a ratio is compared to published tables which reflect the amount of risk for certain diseases or conditions associated with visceral obesity. The waist measurement, i.e., belt size, can also be used by itself. Changes in visceral fat levels in a subject (e.g., a "decrease in visceral fat") in response to treatment can be determined by a subject's waist-to-hip measurement ratio. The waist measurement (or "abdominal perimeter") takes into account both visceral and subcutaneous fat, while the hip measurement takes into account only subcutaneous fat.

Visceral fat can be also assessed both qualitatively and quantitatively, by standard assays known to one of ordinary skill in the art, for example, by computer tomography (CT) scans of, for example, the abdomen. Where desired, CT scans can be used to assess both visceral and subcutaneous fat. In such instances, it can be useful to determine the ratio of visceral fat to subcutaneous fat as part of determination of whether a subject is amenable to therapy, and/or to monitor therapy according to the invention. Visceral fat can be assessed by CT scanning in a single tomographic slice at the $L_4$-$L_5$ level. Visceral fat can be assessed at least partially by analyzing one or more of a magnetic resonance imaging scan and an ultrasonogram.

Normal subjects, i.e., those not displaying obesity, large amounts of visceral fat, or a visceral-fat disease, condition or disorder, who can be amenable to the methods and compositions of the invention can be identified by any method for predicting obesity, visceral fat, or a visceral-fat disease, condition or disorder, including, but not limited to, genetic tests and screening of family histories.

The patient can be suffering from a visceral-fat condition. For example, the patient can be suffering from, or at risk of suffering from, one or more of coronary heart disease, certain cancers, diabetes, glucose intolerance, hyperinsulinemia, hypertension, periodontal disease, metabolic abnormalities, and diabetes. The condition can be related to the patient being overweight. The condition can also be inhibited by weight loss. In some embodiments, the patient is being administered a different medication which causes an increase in relative or absolute values of visceral fat.

Naltrexone and bupropion compositions suitable for use in the present invention include compositions in which the active ingredients are contained in an amount effective to achieve its intended purpose. A "therapeutically effective amount" refers to that amount of the naltrexone and/or bupropion composition that is sufficient to treat or manage a visceral fat condition, typically as determined by a clinician or a physician. In some embodiments, two or more compounds are provided separately or in a single dosage form. In these embodiments, a therapeutically effective amount can be determined based on the combined effects of the two or more compounds. For example, naltrexone and bupropion can be administered at dosages for which the combination of naltrexone and bupropion is effective in decreasing visceral fat content, though the dosages would be ineffective if either naltrexone or bupropion were administered alone. In an embodiment, the amounts of naltrexone and bupropion are selected so that the combination provides an effect that is greater than additive, e.g., synergistically effective, in decreasing visceral fat content and/or metabolic syndrome, as compared to the effect of either naltrexone or bupropion administered alone.

The exact formulation, route of administration and dosage for the naltrexone and bupropion compositions described herein can be chosen by the individual physician in view of the patient's condition. See e.g., Fingl et al. 1975, in "The Pharmacological Basis of Therapeutics", Ch. 1 p. 1.

The naltrexone and/or bupropion can be administered in a controlled-release dosage form, e.g. a sustained-release form. The naltrexone and/or bupropion can be administered to the patient before, during, or after a specific meal or before, during, or after every meal. The composition or compound can be administered before the patient goes to sleep or in the morning. Bupropion can be provided in various dosages, preferably in the range of from about 100 mg to about 600 mg. Examples of bupropion dosages include about 50 mg, about 100 mg, about 150 mg, about 200 mg, about 250 mg, about 300 mg, about 350 mg, about 400 mg, about 450 mg, about 500 mg, about 550 mg or about 600 mg. Naltrexone can also be provided in various dosages, preferably in the range of from about 4 mg to about 50 mg. Examples of naltrexone dosages include about 8 mg, about 16 mg, about 32 mg, about 48 mg, or about 64 mg.

EXAMPLES

Example 1

A double-blind, placebo-controlled multi-center trial was conducted with 285 healthy, non-diabetic, obese subjects. The subjects were administered either bupropion 200 mg bid, placebo (P), naltrexone 48 mg qd ($N_1$), or bupropion 400 mg with naltrexone 32 mg qd ($BN_2$). 182 subjects completed 24 weeks of treatment. A subset of 60 subjects had dual energy X-ray absorptometry (DEXA) and multi-slice CT scans to measure body fat, lean tissue and visceral fat (American Diabetes Association Annual Meeting 2007).

The groups were matched at baseline. Markers of insulin resistance improved more with $BN_2$ than expected from the weight loss alone. A robust effect on decreasing visceral fat was also evident.

TABLE 1

|  | Placebo | Naltrexone 48 mg | Bupropion 400 mg | Naltrexone & Bupropion 32/400 mg |
|---|---|---|---|---|
| Weight (%) | −1.1 ± 0.6*** | −1.74 ± 0.9*** | −3.14 ± 0.7*** | −7.1 ± 0.7 |
| Waist (cm) | −1.0 ± 5.4** | −3.8 ± 12.7 | −2.9 ± 6.0 | −5.4 ± 7.6 |
| Fasting Glucose (mg/dL) | 1.9 ± 1.3* | 3.4 ± 1.7* | 3.5 ± 1.5* | −2.0 ± 1.5 |
| Insulin (mcU/mL) | 0.9 ± 0.9** | 1.7 ± 1.3** | −0.5 ± 1.1 | −3.0 ± 1.1 |
| Triglyceride (mg/dL) | −15.0 ± 7.7* | −17.6 ± 10.4 | −18.4 ± 9.0* | −43.6 ± 8.8 |
| Visceral fat (%) | −4.6 ± 0.6** | −0.1 ± 8.7*** | −2.3 ± 5.1* | −13.7 ± 11.7 |

*$p < 0.05$,
**$p < 0.01$,
***$p < 0.001$

Example 2

Subjects (n=117) received one of six treatments: two placebos (P+P), placebo and naltrexone (P+Nal), bupropion and placebo (Bup+P), bupropion and naltrexone 48 mg (Bup+Nal 48), bupropion and naltrexone 32 mg (Bup+Nal 32), or bupropion and naltrexone 16 mg (Bup+Nal 16).

Subjects had a DEXA body scan to measure total body fat, lean tissue and bone mineral content at baseline and at 6 months. Subjects also had a multi-slice CT scan to determine visceral fat volume at the same time points. The mass of selective visceral loss can be calculated based on total fat and the volume of visceral fat.

The average change in visceral body mass is shown in FIG. 1 for the four treatments. Patients receiving Bup+Nal 32 experienced a dose-related loss in visceral body mass. Statistically significant improvements were also observed in several important metabolic parameters including: plasma glucose, serum insulin and plasma triglycerides.

TABLE 2

Baseline Weight, BMI and Weight Circumference

|  | P + P | P + Nal | Bup + P | Bup + Nal 48 | Bup + Nal 32 | Bup + Nal 16 |
|---|---|---|---|---|---|---|
| Weight (kg) Mean | 98.8 | 96.3 | 101.4 | 92.9 | 98.3 | 92.7 |
| BMI (kg/m2) Mean | 34.7 | 35.3 | 35.8 | 34.0 | 35.1 | 34.4 |
| Waist Circumference (cm) | 105.8 | 104.3 | 107.7 | 102.1 | 103.5 | 102.0 |

TABLE 2-continued

Baseline Weight, BMI and Weight Circumference

|  | P + P | P + Nal | Bup + P | Bup + Nal 48 | Bup + Nal 32 | Bup + Nal 16 |
|---|---|---|---|---|---|---|
| Change in Waist Circumference (cm) | — | −1.5 | 1.9 | −3.7 | −2.3 | −3.8 |
| Change in Waist Circumference (%) vs. placebo | — | −1.4 | 1.8 | −3.5 | −2.2 | −3.6 |

TABLE 3

Change from Baseline, Visceral Adipose Mass

|  | P + P | P + Nal | Bup + P | Bup + Nal 48 | Bup + Nal 32 | Bup + Nal 16 | Bup + Nal # |
|---|---|---|---|---|---|---|---|
| Change from Baseline Mean (SD), Visceral Adipose Mass | −4.6 (9.6) | −0.1 (8.7) | −2.3 (5.1) | −16.7 (15.2) | −13.7 (11.7) | −15.5 (14.9) | −14.7 (12.9) |
| P-Value* | 0.064 | 0.971 | −.278 | 0.027 | <0.001 | 0.009 | <0.001 |
| LS Mean (SE)^ | −1.2 (2.7) | 3.5 (3.5) | 0.2 (4.3) |  |  |  | −11.0 (2.1) |
| P-value (vs. B + N)* | 0.003 | <0.001 | 0.024 |  |  |  |  |

TABLE 4

Change from Baseline, Total Body Adipose Mass

|  | P + P | P + Nal | Bup + P | Bup + Nal 48 | Bup + Nal 32 | Bup + Nal 16 | Bup + Nal # |
|---|---|---|---|---|---|---|---|
| Change from Baseline Mean (SD), Total Body Adipose Mass | −4.0 (7.1) | −3.2 (6.9) | −4.1 (4.1) | −15.7 (13.2) | −12.2 (8.4) | −16.0 (8.4) | −13.7 (9.3) |
| P-Value* | 0.035 | 0.150 | 0.026 | 0.020 | <0.001 | <0.001 | <0.001 |
| LS Mean (SE)^ | −1.9 (2.2) | −1.5 (2.7) | −2.6 (3.1) |  |  |  | −11.0 (1.7) |
| P-value (vs. B + N)* | <0.001 | <0.001 | 0.010 |  |  |  |  |

TABLE 5

Metabolic Parameters

|  | Placebo | Naltrexone | Bupropion | Bup + Nal 32 |
|---|---|---|---|---|
| Plasma Glucose (mg/dL) | 1.9 ± 1.3* | 3.4 ± 1.7** | 3.5 ± 1.5** | −2.0 ± 1.5 |
| Serum Insulin (uU/mL) | 0.9 ± 0.9*** | 1.7 ± 1.3*** | −0.5 ± 1.1 | −3.0 ± 1.1 |
| Triglycerides (mg/dL) | −15.0 ± 7.7** | −17.6 ± 10.4 | −18.4 ± 9.0 | −43.6 ± 8.8 |

The results demonstrate that weight loss associated with Bup+Nal 32 was essentially due to decreased adipose tissue, as opposed to lean tissue. The percentage of this decrease was similar in magnitude in both visceral and overall adipose tissue. Visceral adipose tissue loss indicates that the combination of bupropion and naltrexone (e.g., Bup+Nal 32) will likely benefit cardio-vascular risk factors associated with obesity. Bupropion and naltrexone 32 mg showed a synergistic effect for weight loss and loss of visceral adipose mass. The change in the total adipose mass and visceral adipose mass associated with Bup+Nal 48 was not significant. However, the group of patients receiving Bup+Nal 48 had a higher early drop-out rate which reduced the sample size, thereby affecting the significance calculations.

Metabolic syndrome represents a group of risk factors that have been linked to obesity, insulin resistance and are present in about 47 million Americans. This syndrome can increase the risk of later developing diabetes or cardiovascular disease and can be reduced by a loss in excess body weight.

A post-hoc evaluation was applied on the baseline prevalence of the metabolic syndrome among 361 evaluable subjects, as defined by the Adult Treatment Panel III Guidelines. Approximately one in three study subjects were determined to have exhibited the metabolic syndrome at baseline. Treatment with bupropion and naltrexone was associated with a significantly higher rate of subjects who no longer met metabolic syndrome criteria after 24 weeks of treatment than seen with placebo (p=0.04). Subjects were administered the same treatments as described in Example 2. Of the bupropion and naltrexone dosage forms, Bup+Nal 32 demonstrated the best overall risk to benefit ratio with a decrease in metabolic syndrome from 30% to 14% using a conservative ITT-LOCF analysis (p<0.05). Improvements associated with the Bup+Nal 32 treatment across the parameters defining metabolic syndrome were most dramatic on reductions in triglycerides (0.6% P+P, −33.6% Bup+Nal 32, p<0.01) and waist circumference (−1.8% P+P, −6.4% Bup+Nal 32, p=0.06) while also favorably increasing HDL cholesterol (0.3% P+P, 15.1% Bup+Nal 32, p<0.01). The increase in HDL cholesterol is especially noteworthy since the literature indicates that a 1% increase in HDL cholesterol leads to a 2% reduction in cardiovascular risk. These data indicate that bupropion and naltrexone dosage forms described herein, particularly the 32/400 dose, reduce the metabolic syndrome prevalence and improve cardiovascular risk amongst those individuals with the greatest need for risk reduction. Treatment with bupropion and naltrexone significantly decreased the percent of the study population with the metabolic syndrome from 31% to 15% in the pooled NB groups as compared to only a 38% to 30% within the placebo cohort (p=0.04).

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A method of improving markers of insulin resistance comprising administering to a person who has been identified or diagnosed as being in need thereof an amount of naltrexone or a pharmaceutically acceptable salt thereof in a range of about 4 mg to about 50 mg each day and an amount of bupropion or a pharmaceutically acceptable salt thereof in a range of about 100 mg to about 600 mg each day, wherein the improvement in markers of insulin resistance is greater than expected from weight loss alone.

2. The method of claim 1, wherein the amount of bupropion or a pharmaceutically acceptable salt thereof is about 400 mg, and the amount of naltrexone or a pharmaceutically acceptable salt thereof is about 32 mg.

3. The method of claim 1, wherein the amount of naltrexone or a pharmaceutically acceptable salt thereof and the amount of bupropion or a pharmaceutically acceptable salt thereof are administered together in a single dosage form.

4. The method of claim 1, wherein naltrexone or a pharmaceutically acceptable salt thereof is in a sustained-release form, and bupropion or a pharmaceutically acceptable salt thereof is in a sustained-release form.

5. A method of improving fasting blood glucose levels comprising administering to a person who has been identified or diagnosed as being in need thereof an amount of naltrexone or a pharmaceutically acceptable salt thereof in a range of about 4 mg to about 50 mg each day and an amount of bupropion or a pharmaceutically acceptable salt thereof in a range of about 100 mg to about 600 mg each day, wherein the improvement in fasting blood glucose is significantly greater than expected from naltrexone or bupropion alone.

6. The method of claim 5, wherein the amount of bupropion or a pharmaceutically acceptable salt thereof is about 400 mg, and the amount of naltrexone or a pharmaceutically acceptable salt thereof is about 32 mg.

7. The method of claim 5, wherein the amount of naltrexone or a pharmaceutically acceptable salt thereof and the amount of bupropion or a pharmaceutically acceptable salt thereof are administered together in a single dosage form.

8. The method of claim 5, wherein naltrexone or a pharmaceutically acceptable salt thereof is in a sustained-release form, and bupropion or a pharmaceutically acceptable salt thereof is in a sustained-release form.

9. The method of claim 5, wherein fasting blood glucose is reduced to less than about 110 mg/dL.

10. A method of improving triglyceride levels or high-density cholesterol levels comprising administering to a person who has been identified or diagnosed as being in need thereof an amount of naltrexone or a pharmaceutically acceptable salt thereof in a range of about 4 mg to about 50 mg each day and an amount of bupropion or a pharmaceutically acceptable salt thereof in a range of about 100 mg to about 600 mg each day.

11. The method of claim 10, wherein the amount of bupropion or a pharmaceutically acceptable salt thereof is about 400 mg, and the amount of naltrexone or a pharmaceutically acceptable salt thereof is about 32 mg.

12. The method of claim 10, wherein the amount of naltrexone or a pharmaceutically acceptable salt thereof and the amount of bupropion or a pharmaceutically acceptable salt thereof are administered together in a single dosage form.

13. The method of claim 10, wherein naltrexone or a pharmaceutically acceptable salt thereof is in a sustained-release form, and bupropion or a pharmaceutically acceptable salt thereof is in a sustained-release form.

14. The method of claim 10, wherein the method improves triglyceride levels and the improvement is greater than expected from naltrexone or bupropion alone.

15. The method of claim 10, wherein the method improves high-density cholesterol levels.

16. The method of claim 14, wherein triglyceride levels are reduced to less than about 150 mg/dL.

17. The method of claim 15, wherein the person is male and high-density cholesterol levels are increased to more than about 40 mg/dL.

18. The method of claim 15, wherein the person is female and high-density cholesterol levels are increased to more than about 50 mg/dL.

* * * * *